(12) United States Patent
Ruebeck

(10) Patent No.: US 12,357,310 B2
(45) Date of Patent: Jul. 15, 2025

(54) DEVICE AND METHOD FOR CONNECTING TUBULAR STRUCTURES

(71) Applicant: David Ruebeck, Minneapolis, MN (US)

(72) Inventor: David Ruebeck, Minneapolis, MN (US)

(73) Assignee: David Ruebeck, Minneapolis, MN (US)

( * ) Notice: Subject to any disclaimer, the term of this patent is extended or adjusted under 35 U.S.C. 154(b) by 0 days.

(21) Appl. No.: 18/603,080

(22) Filed: Mar. 12, 2024

(65) Prior Publication Data

US 2024/0215982 A1    Jul. 4, 2024

Related U.S. Application Data

(63) Continuation of application No. 17/456,541, filed on Nov. 24, 2021, now Pat. No. 11,950,782, which is a continuation of application No. 16/383,469, filed on Apr. 12, 2019, now Pat. No. 11,219,459.

(60) Provisional application No. 62/659,075, filed on Apr. 17, 2018.

(51) Int. Cl.
*A61B 17/11* (2006.01)
*A61F 2/06* (2013.01)

(52) U.S. Cl.
CPC ... *A61B 17/1114* (2013.01); *A61B 2017/1107* (2013.01); *A61B 2017/1132* (2013.01); *A61B 2017/1135* (2013.01); *A61F 2/064* (2013.01)

(58) Field of Classification Search
CPC ......... A61B 17/1114; A61B 2017/1107; A61B 2017/1132; A61B 2017/1135
See application file for complete search history.

(56) References Cited

U.S. PATENT DOCUMENTS

| | | | |
|---|---|---|---|
| 4,214,587 A | * | 7/1980 | Sakura, Jr. ............. A61B 17/11 623/1.1 |
| 5,366,462 A | | 11/1994 | Kaster et al. |
| 5,695,504 A | | 12/1997 | Gifford, III et al. |
| 6,193,734 B1 | | 2/2001 | Bolduc et al. |
| 6,451,034 B1 | | 9/2002 | Gifford, III et al. |
| 6,629,988 B2 | | 10/2003 | Weadock |
| 6,776,785 B1 | | 8/2004 | Yencho et al. |
| 7,022,131 B1 | | 4/2006 | Derowe et al. |
| 7,048,747 B2 | | 5/2006 | Arcia et al. |
| 7,063,711 B1 | | 6/2006 | Loshakove et al. |
| 7,497,865 B2 | | 3/2009 | Willis et al. |
| 7,819,895 B2 | | 10/2010 | Ginn et al. |

(Continued)

FOREIGN PATENT DOCUMENTS

WO    WO 2001/041623 A2    6/2001
WO    WO 2001/041623 A3    6/2001

OTHER PUBLICATIONS

WIPO, U.S. International Search Authority, International Search Report and Written Opinion mailed Jul. 5, 2019 in International Patent Application No. PCT/US2019/027375, 9 pages.

(Continued)

*Primary Examiner* — Phong Son H Dang
(74) *Attorney, Agent, or Firm* — Inskeep IP Group, Inc.

(57) ABSTRACT

A device and method for performing anastomosis is described. In one embodiment according to the present invention, the device comprises a ring that has a plurality of pins extending from various locations on the ring. During a procedure, the pins are passed through portions of tissue and the ring is everted or radially flipped inside out to connect the tissues together.

20 Claims, 27 Drawing Sheets

(56) References Cited

U.S. PATENT DOCUMENTS

| | | | |
|---|---|---|---|
| 8,303,609 | B2 | 11/2012 | Lentz et al. |
| 8,690,910 | B2 | 4/2014 | Carley et al. |
| 8,920,442 | B2 | 12/2014 | Sibbitt, Jr. et al. |
| 9,414,822 | B2 | 8/2016 | Ziobrio et al. |
| 10,245,013 | B2 * | 4/2019 | Carley ................ A61B 17/068 |
| 11,826,029 | B2 | 11/2023 | Hong et al. |
| 2004/0002721 | A1 | 1/2004 | Podmore et al. |
| 2004/0030348 | A1 | 2/2004 | Peterson et al. |
| 2005/0070939 | A1 | 3/2005 | Beaupre |
| 2005/0288693 | A1 | 12/2005 | Suyker et al. |
| 2007/0282352 | A1 | 12/2007 | Carley et al. |
| 2008/0027481 | A1 | 1/2008 | Gilson et al. |
| 2008/0319475 | A1 | 12/2008 | Clark et al. |
| 2010/0106172 | A1 | 4/2010 | Suyker et al. |
| 2010/0249920 | A1 | 9/2010 | Bolling et al. |
| 2012/0245603 | A1 | 9/2012 | Voss |
| 2015/0250461 | A1 | 9/2015 | Berreklouw |
| 2015/0313599 | A1 | 11/2015 | Johnson et al. |
| 2019/0209352 | A1 | 7/2019 | Wilger et al. |

OTHER PUBLICATIONS

European Patent Office, Extended European Search Report dated Nov. 26, 2021 in European Patent Application No. 19789105.4, 8 pages.

* cited by examiner

DEVICE AND METHOD FOR CONNECTING TUBULAR STRUCTURES

RELATED APPLICATIONS

This application is a continuation of patent application Ser. No. 17/456,541, filed Nov. 24, 2021, entitled Device And Method For Connecting Tubular Structures, which is a continuation of patent application Ser. No. 16/383,469, filed Apr. 12, 2019, entitled Device And Method For Connecting Tubular Structures (now U.S. Pat. No. 11,219,459), which claims benefit of and priority to U.S. Provisional Application Ser. No. 62/659,075 filed Apr. 17, 2018 entitled Device and Method for Connecting Tubular Structures, all of which are hereby incorporated herein by reference in their entireties.

BACKGROUND OF THE INVENTION

Many different medical procedures require a surgical connection between two cavities or passages, such as blood vessels, ducts, prosthetic tubes, intestines, or portions of the urinary tract. This connection procedure is often referred to as anastomosis.

Commonly, anastomosis procedures are performed by hand suturing, mechanical connection, biological glues, or a combination thereof. The connection technique often depends on the types of passages/cavities being joined (e.g., blood vessels or intestines), the angle of connection (e.g., an end-to-end connection or a lateral, end-to-side connection), the size of the passages (e.g., less than 1 mm in diameter to over 25 mm), and whether different types of structures are being connected (e.g., a bladder and urethra).

Hand-sewn sutures tend to be used most frequently because their suitability, regardless of the type of structures being connected, size, or the angle of connection. Sutures can also be easily removed during a procedure if initially connected in an undesirable manner. However, suturing often requires a significant amount of time to perform during a procedure. Additionally, proper surgical suturing techniques for anastomosis require a significant amount of training for the surgeon, and frequently require a trained assistant during a procedure. Occasionally, sutured anastomoses can also be complicated by stricture.

Staples or other mechanical closure devices are often desirable due to their ability to quickly connect two structures during a procedure. However, relatively large and complicated devices are typically required, which can limit what types of closure sizes and structures can be connected. Similarly, biological glues are desirable due to their ability to quickly connect two tissue structures, but often cannot be easily dissolved if the initial connection was undesirable.

In this respect, there remains a need for an anastomosis closure device that can quickly connect two structures together, provides a reversible connection, is more reliable and easier to deploy than sutures, and can be used with a wide range of shapes/sizes of biological structures.

SUMMARY OF THE INVENTION

The present invention is generally directed to a device and method for performing anastomosis. In one embodiment according to the present invention, the device comprises a ring that has a plurality of pins extending from various locations on the ring. During a procedure, the pins are passed through portions of tissue and the ring is everted or radially flipped inside out to connect the tissues together.

In one embodiment, the device includes a ring formed of a plurality of alternating curves or wave shapes. In one embodiment, the ring is shaped to allow eversion or outward rotation. In one embodiment, the device comprises a plurality of alternating, curved pins. In another embodiment, the device comprises a plurality of relatively short pins. In another embodiment the device comprises a plurality of relatively long pins.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
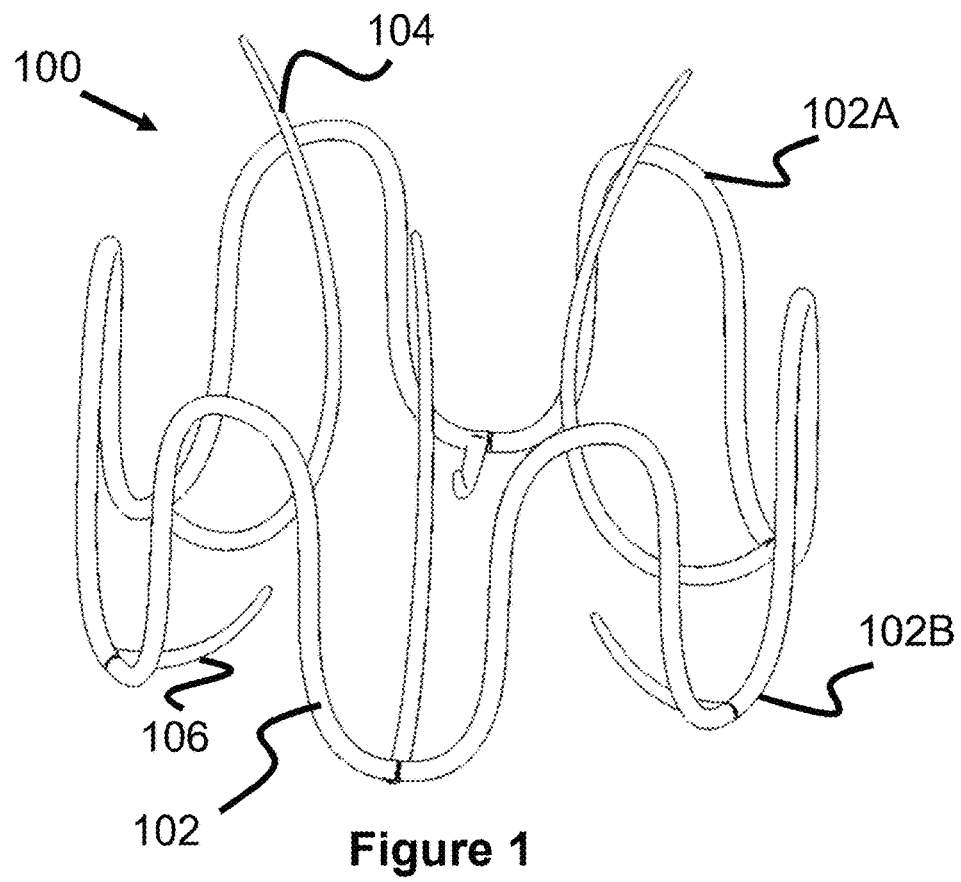
FIG. 1 illustrates a perspective view of a tubular connection device according to the present invention.
Figure 2:
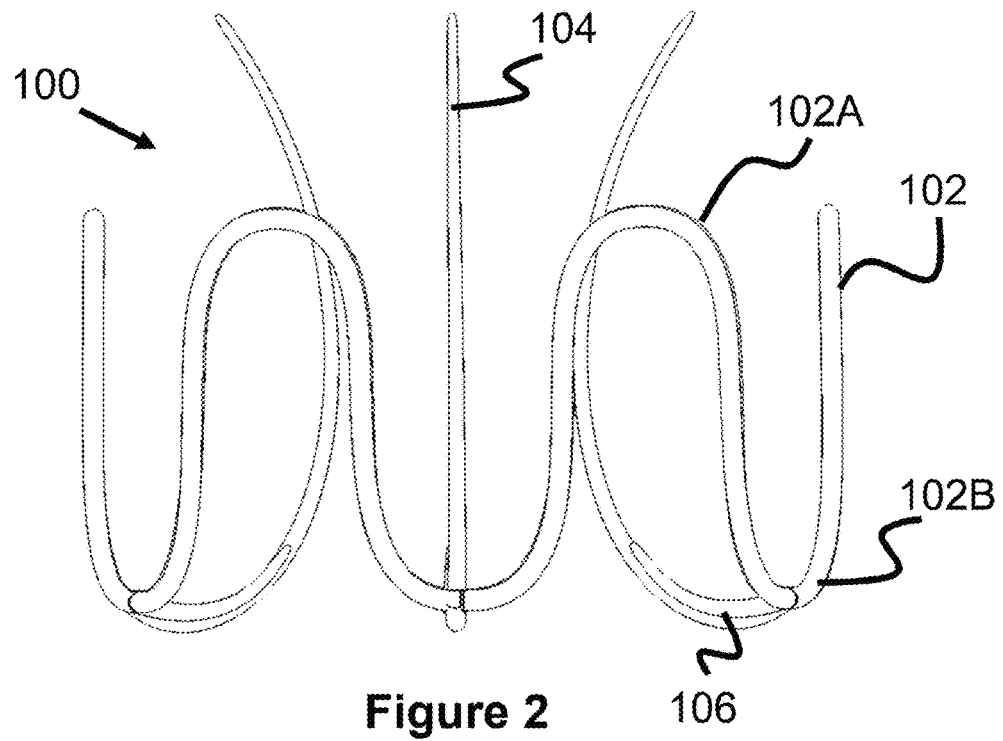
FIG. 2 illustrates a side view of a tubular connection device according to the present invention.
Figure 3:
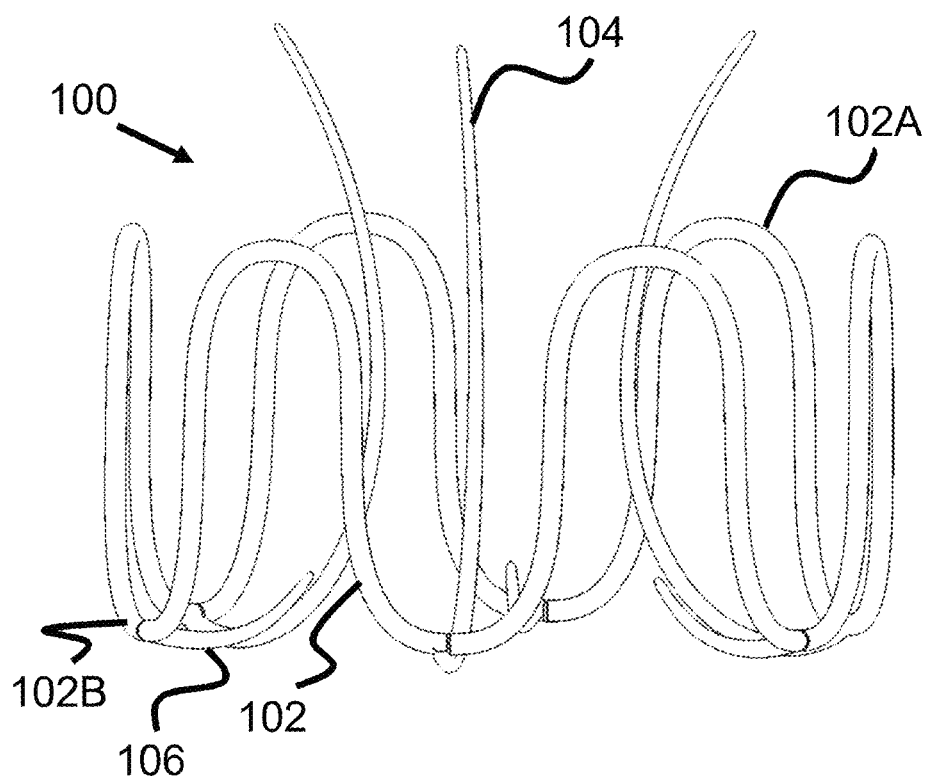
FIG. 3 illustrates a side view of a tubular connection device according to the present invention.
Figure 4:
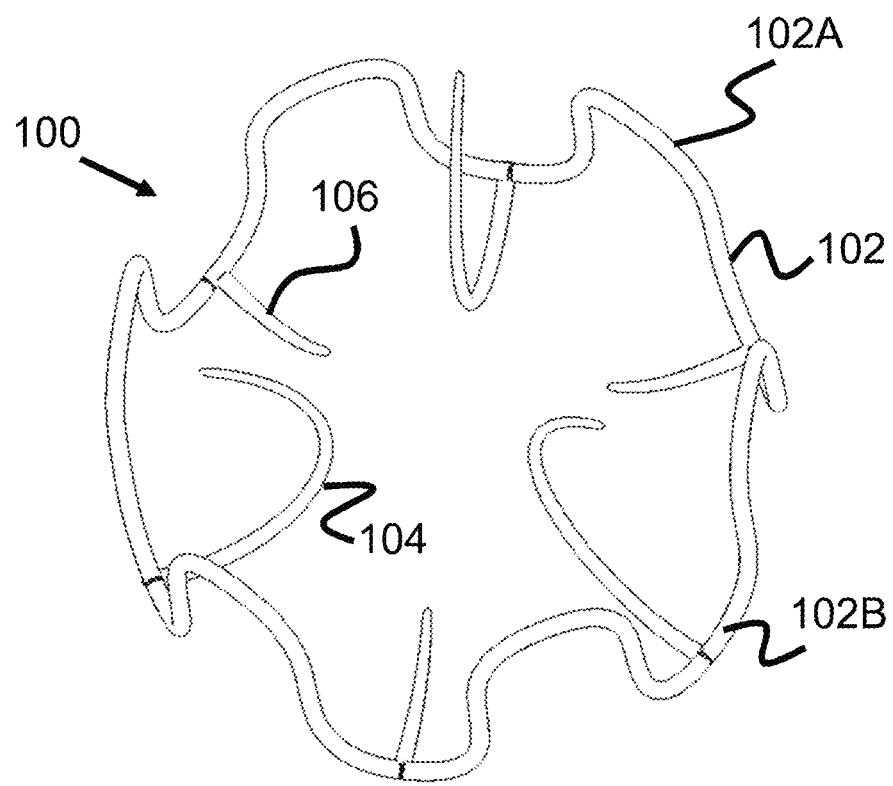
FIG. 4 illustrates a top view of a tubular connection device according to the present invention.

Specific embodiments of the invention will now be described with reference to the accompanying drawings. This invention may however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The present invention is generally directed to a device for performing anastomosis. While the present specification primarily describes the use of the present invention for connecting blood vessels, ducts, intestines, and the urinary tract, it should be understood that it can be used with any biological structures that have passages and/or cavities. The devices of the prevent invention are described as moving from a normal, initial, and/or inverted configuration to an everted configuration. It should be understood that the everted configuration can mean that the device has flipped or has been rotated about its circumference relative to its initial configuration. In some examples, this rotation may be more, less, or about 180 degrees and the device may end up being at least partially inside-out relative to its initial configuration. While eversion (e.g., rotation radially outwards about itself) is described in this specification, it may be possible for some embodiments to achieve similar results by being inverted, especially when only relatively small pins are used.

FIGS. 1-4 illustrate one embodiment according to the present invention of an anastomosis device 100 for connecting biological structures. The device 100 comprises a ring 102 that has a plurality of pins 104, 106 extending from various locations on the ring 102. During a procedure, the pins 104, 106 are used to pass through and initially connect portions of tissue. The ring 102 is then everted or radially flip inside out to press the tissues together, as described further below.

In the present embodiment, the ring 102 is composed of a wire or elongated structure formed into a plurality wave shapes having peaks 102A and troughs 102B. These wave shapes facilitate expansion and contraction of portions of the ring 102 during its eversion process. Preferably, the peaks 102A and troughs 102B have curved or rounded shapes, however other shapes that allow eversion are possible, such as square/rectangular waves, "zig-zag" struts, or even a woven mesh structure. The ring 102 is connected to form an unbroken circular wave structure but may also be formed as a broken C-shape. Additionally, while each of the waves of the ring 102 are depicted as being uniform in size, some waves may be larger than other waves. For example, the ring 102 may have alternating larger and smaller waves. While the term "ring" is used, it should be understood to mean circular/tubular shapes, square shapes, triangular shapes, hexagonal, octagonal, and similar multisided shapes.

The ring 102 and pins 104, 106 may be composed of one or more wires of any shape (e.g., circular, flat, or nonsymmetrical). Preferably, this wire is composed of a shape memory metal (e.g., nitinol), however, other metals or polymers are also possible. In one embodiment, the wire is composed of a bioresorbable material. In another embodiment, the device 100 is laser-cut from a ring of material. In an alternate embodiment, the ring can be composed of a flexible material, such as silicone, and the pins 104, 106 can be composed of a rigid material.

If the device is composed of a shape memory material, it can be configured to have a memory shape (e.g., a heat-set shape) that facilitates its eversion. For example, upon reaching a certain temperature, such as body temperature, the shape memory material may also reach its transition temperature, causing it to twist to its everted shape.

The device 100 includes both elongated pins 104 and shortened pins 106 that are connected at the troughs 102B in an alternating arrangement. The elongated pins 104 preferably have a shape that curves radially inwards, upward, and then radially outward relative to the device 100. In one example, the elongated pins 104 extend above the peaks 102A of the waves but can alternately extend to a height of about that of the peaks 102A or even somewhat below the peaks 102A. The elongated pins 104 form an upward curve within a range of about 90 degrees and 180 degrees, and preferably of about 150 degrees. The shortened pins 106 preferably have a shape that extends radially inwards and upwards relative to the device 100. The shortened pins 106 form an upward curve within a range of about 30 degrees and 90 degrees, and preferably of about 60 degrees. Both pins 104 and 106 preferably have sharpened distal ends shaped to easily pierce tissue. While a barb or similar shape on the distal ends is possible, a uniform, tapered shape is preferred to allow the pins to be removed from tissue for repositioning, if necessary.

Figure 5:
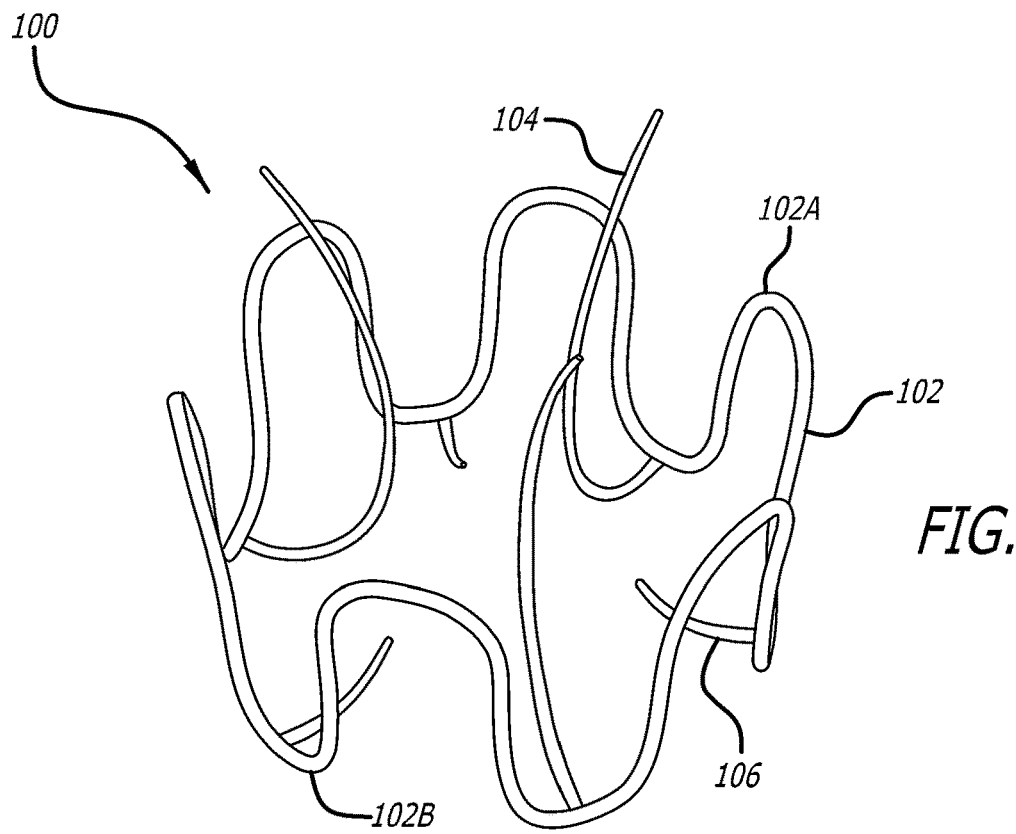
FIG. 5 illustrates the device of FIG. 1 being inverted.
Figure 6:
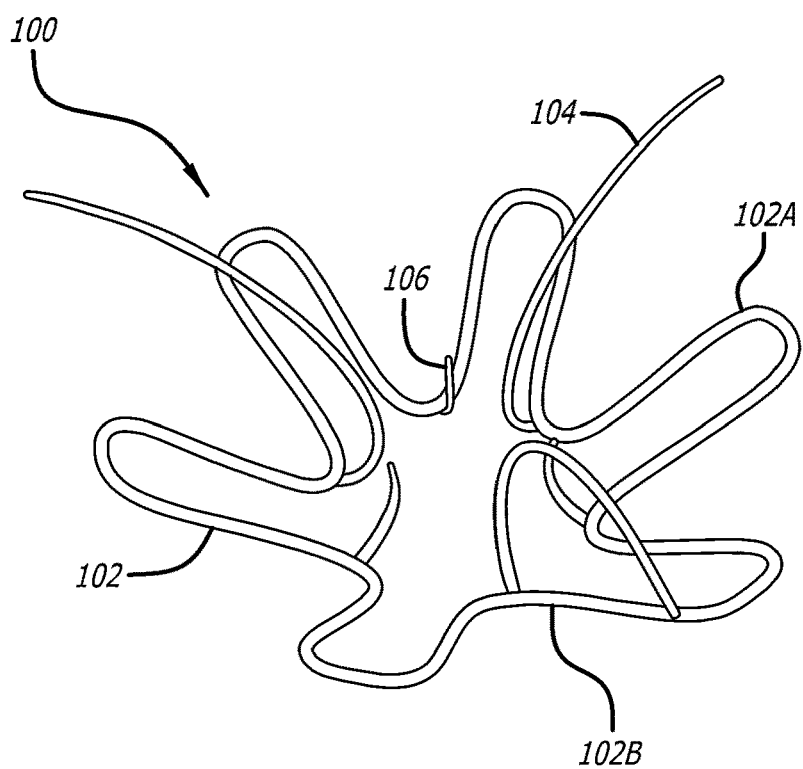
FIG. 6 illustrates the device of FIG. 1 being inverted.

Turning to FIGS. 5-8, the device 100 can be caused to evert during an anastomosis procedure. Note, the eversion is also shown in FIGS. 9-12 with a tubular structure. This eversion process can be performed by hand or with the assistance of deployment tools, as described later in this specification. FIG. 5 illustrates the device 100 in an initial or normal configuration in which the pins 104, 106 are facing radially inwards and upwards relative to the viewer of the figure. In FIG. 6, the peaks 102A of the ring 102 are moved radially outward and downward, causing distal ends of pins 104 to rotate to an upward position and the distal ends of pins 106 to rotate towards an outwardly radial position.

Figure 7:
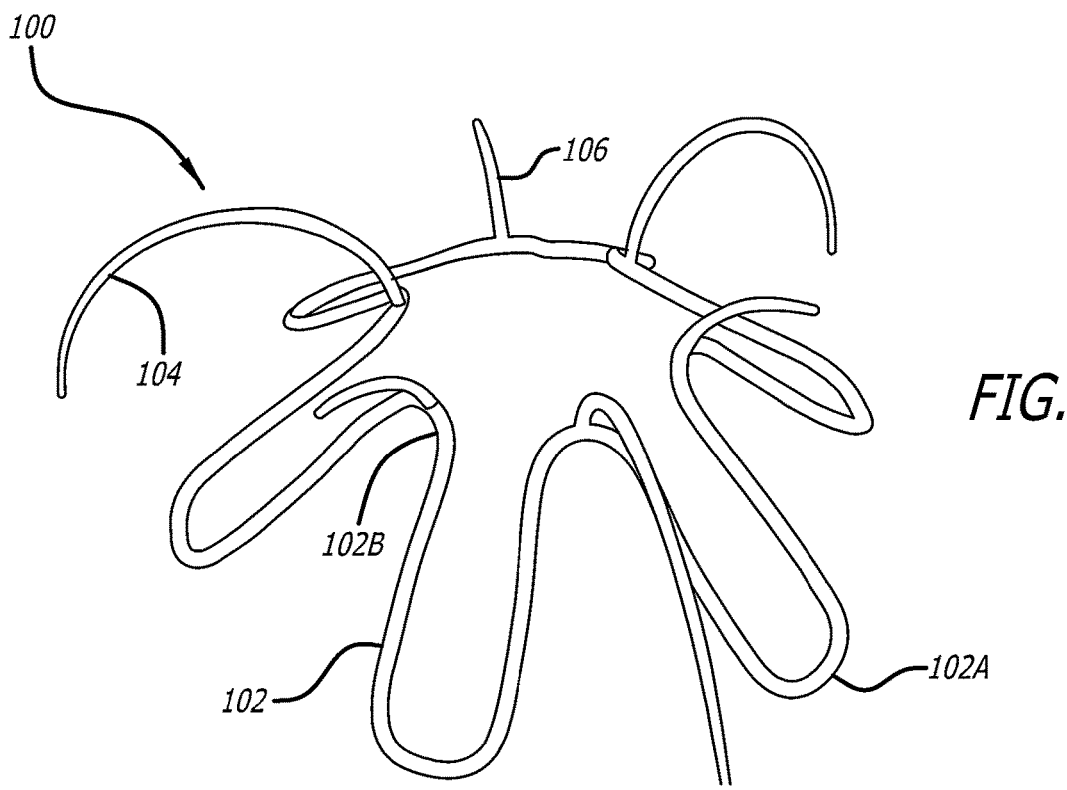
FIG. 7 illustrates the device of FIG. 1 being inverted.
Figure 8:
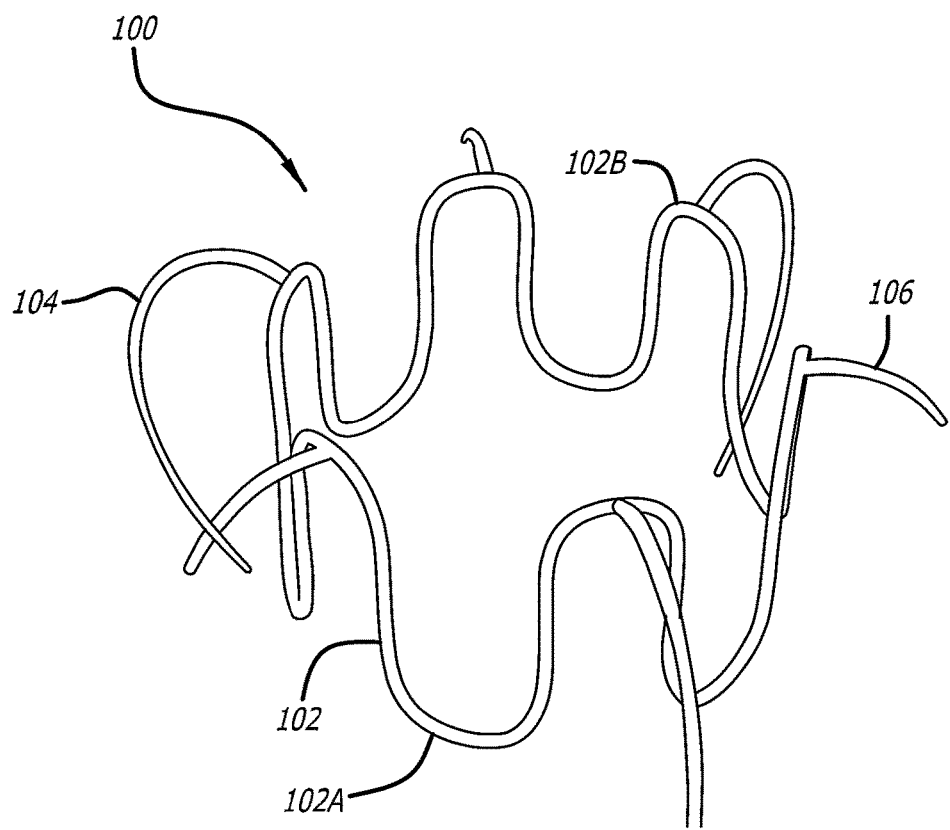
FIG. 8 illustrates the device of FIG. 1 being inverted.
Figure 9:
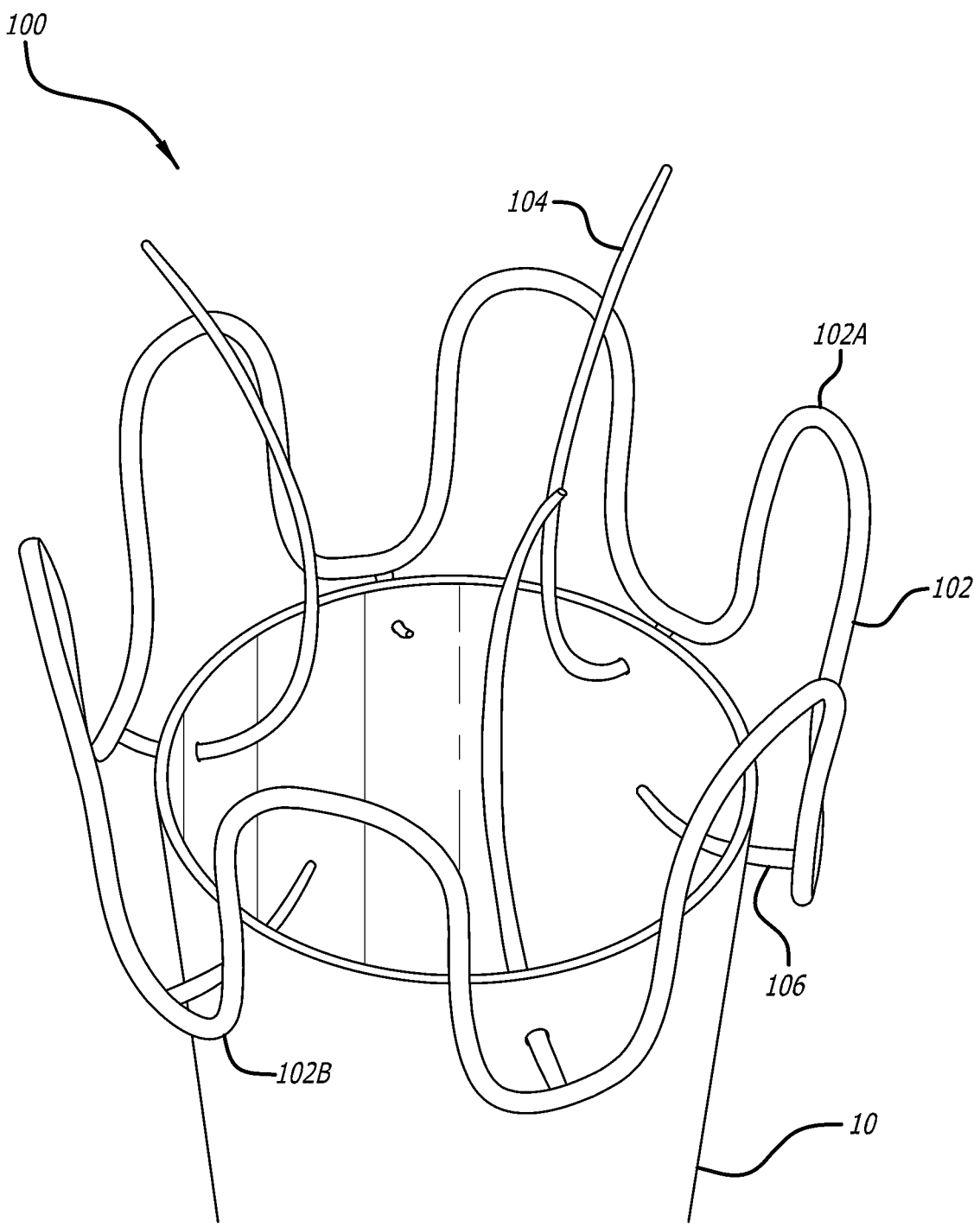
FIG. 9 illustrates the device of FIG. 1 being inverted.
Figure 10:
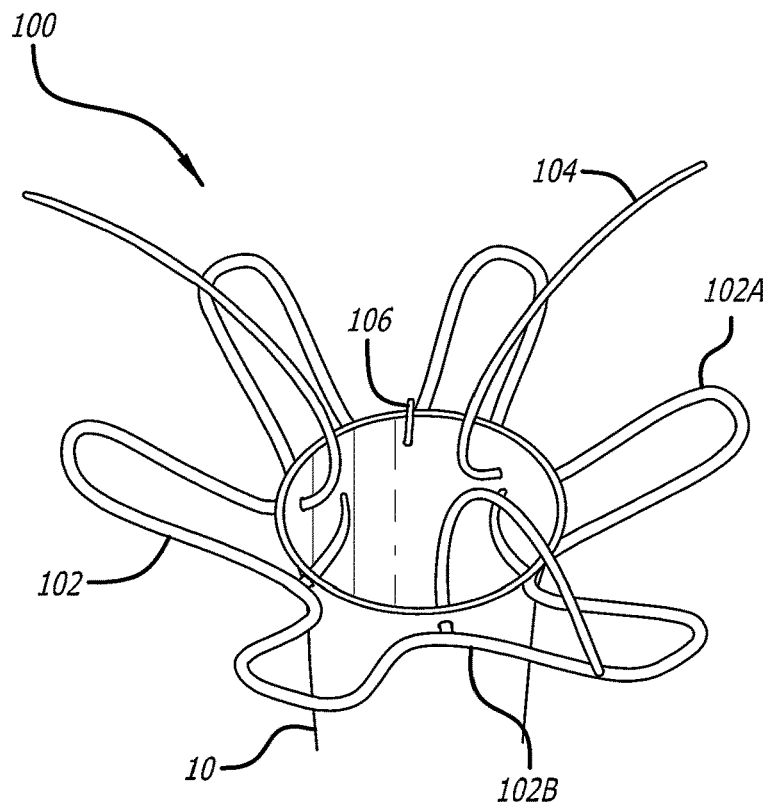
FIG. 10 illustrates the device of FIG. 1 being inverted.
Figure 11:
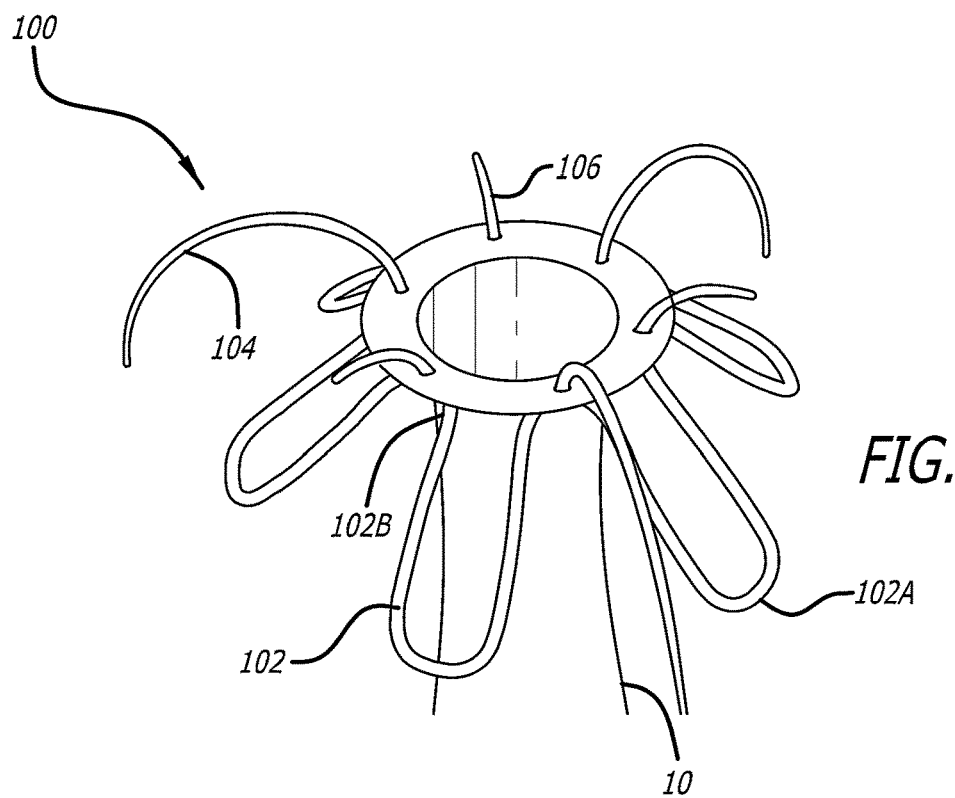
FIG. 11 illustrates the device of FIG. 1 being inverted.
Figure 12:
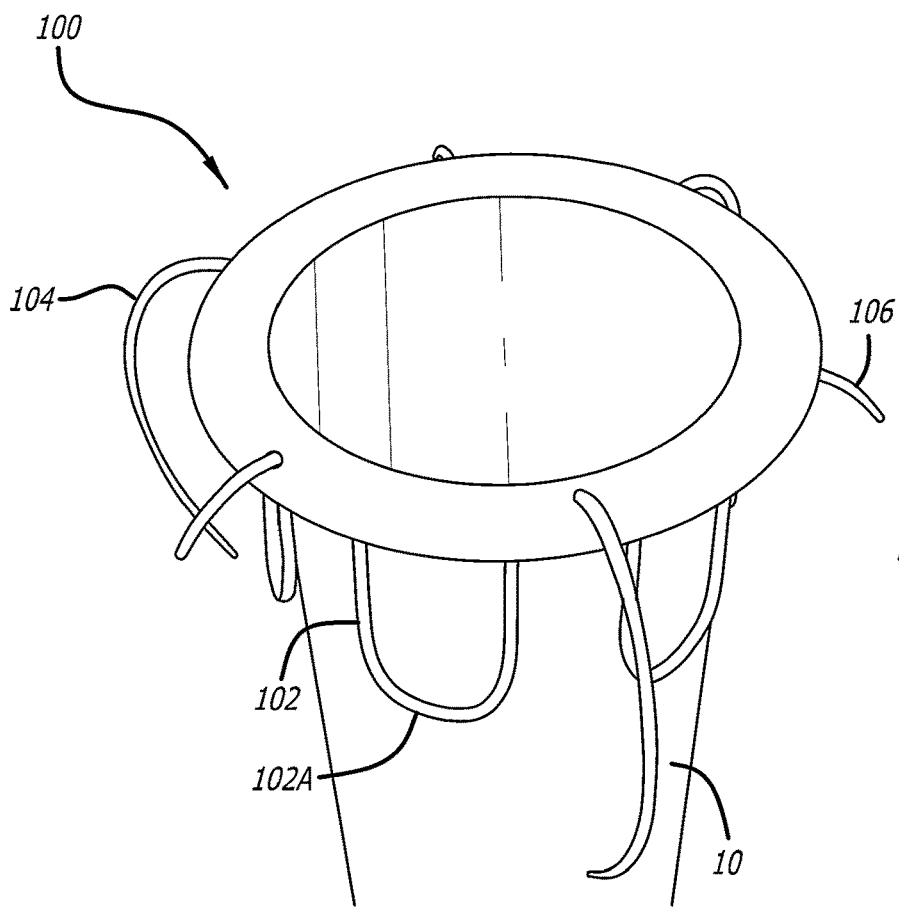
FIG. 12 illustrates the device of FIG. 1 being inverted.
Figure 13:
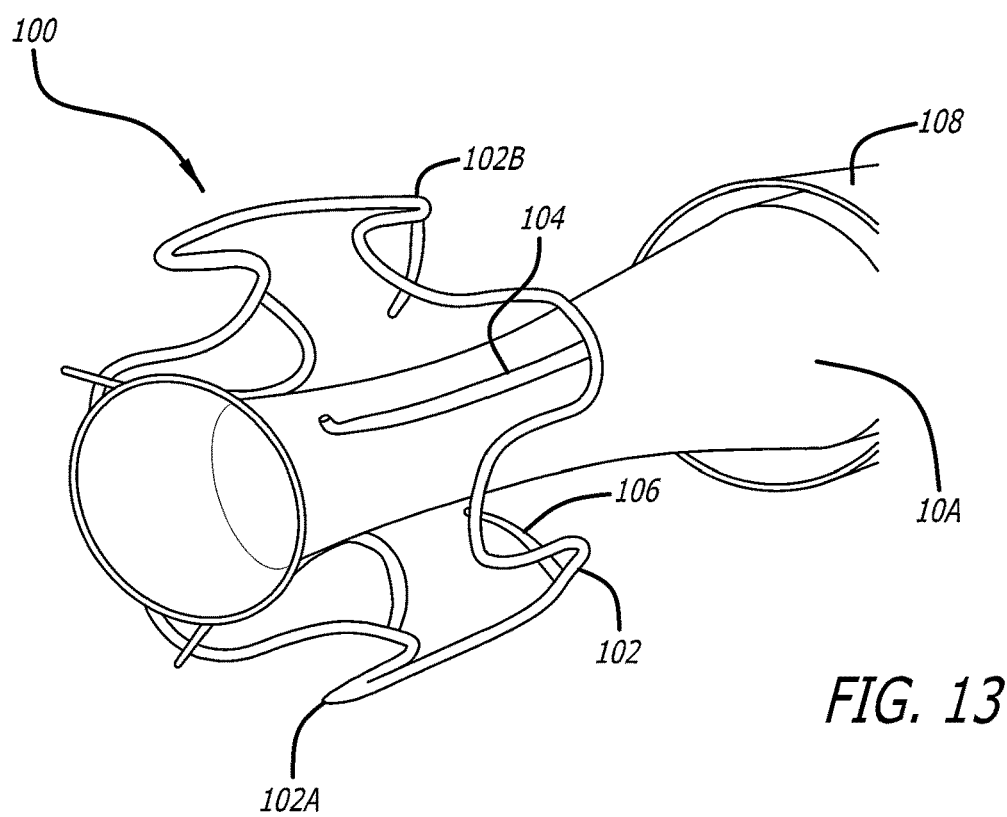
FIG. 13 illustrates the device of FIG. 1 connecting two tubular structures.

In FIG. 7, the peaks 102A of the ring 102 and the distal ends of the pins 104 continue to rotate to a downwardly-angled position. The distal ends of the pins 106 also continue to rotate to an outwardly radial position. Finally, in FIG. 8, the device 100 is completely everted or inside out. In this everted configuration, the troughs 102B and peaks 102A are inverted in height, the pins 106 are angled radially outward from the ring 102, and the pins 104 are angled radially outward and downward from the ring 102.

FIGS. 13-20 illustrate this eversion movement in connection with securing two blood vessel ends during an anastomosis procedure. Beginning with FIG. 9, an optional retaining band 108 is placed over a first vessel 10A, followed by the device 100. The device 100 is oriented such that the peaks 102A are located closest to the end of the vessel 10A.

Figure 14:
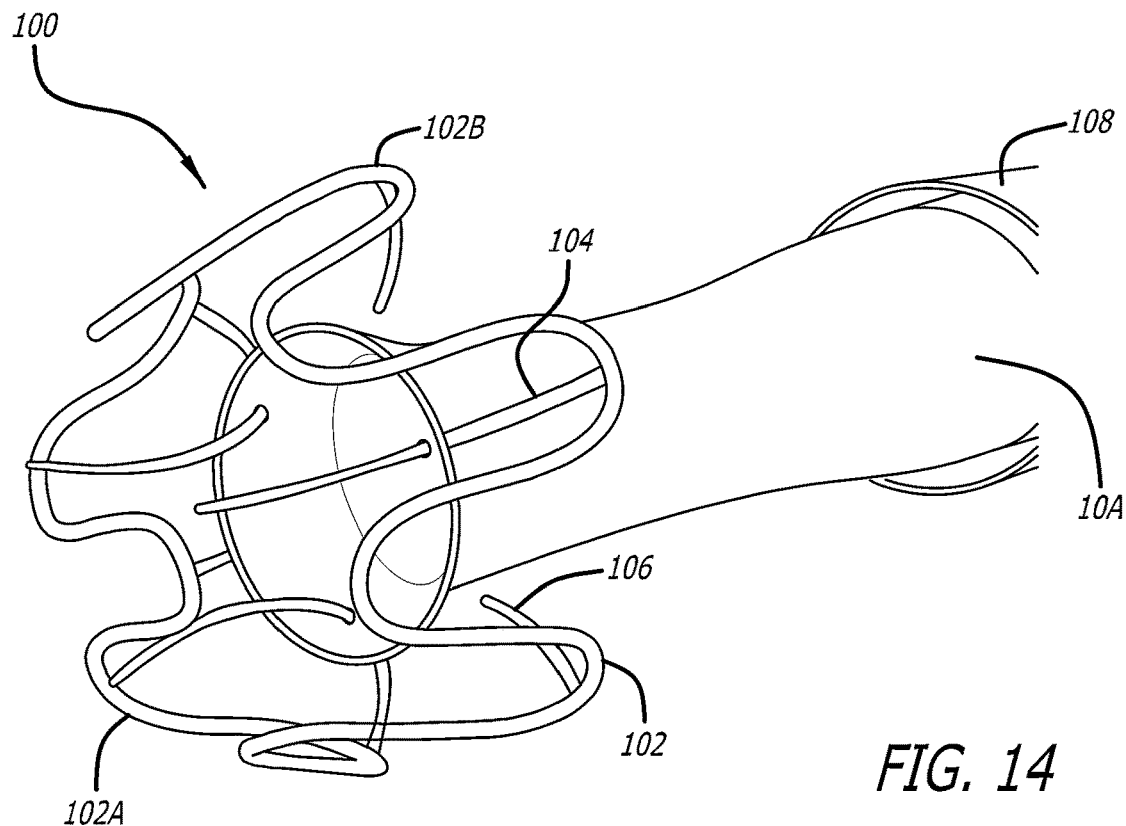
FIG. 14 illustrates the device of FIG. 1 connecting two tubular structures.

In FIG. 14, the elongated pins 104 are inserted through the tissue around the opening of the first vessel 10A. The top end or peaks 102A may be somewhat radially compressed to assist in properly directing the elongated pins 104 through the tissue. As the peaks 102A are radially expanded again, the smaller pins 106 are also directed through the tissue around the opening of the first vessel 10A.

Figure 15:
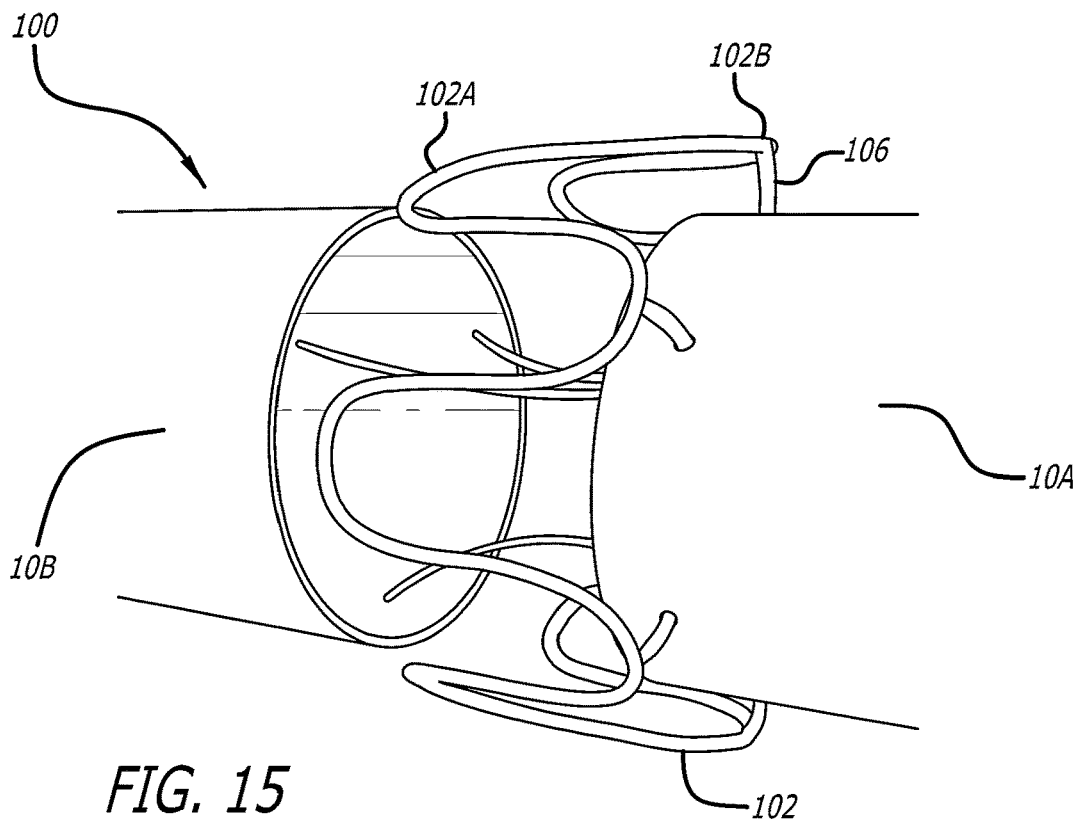
FIG. 15 illustrates the device of FIG. 1 connecting two tubular structures.
Figure 16:
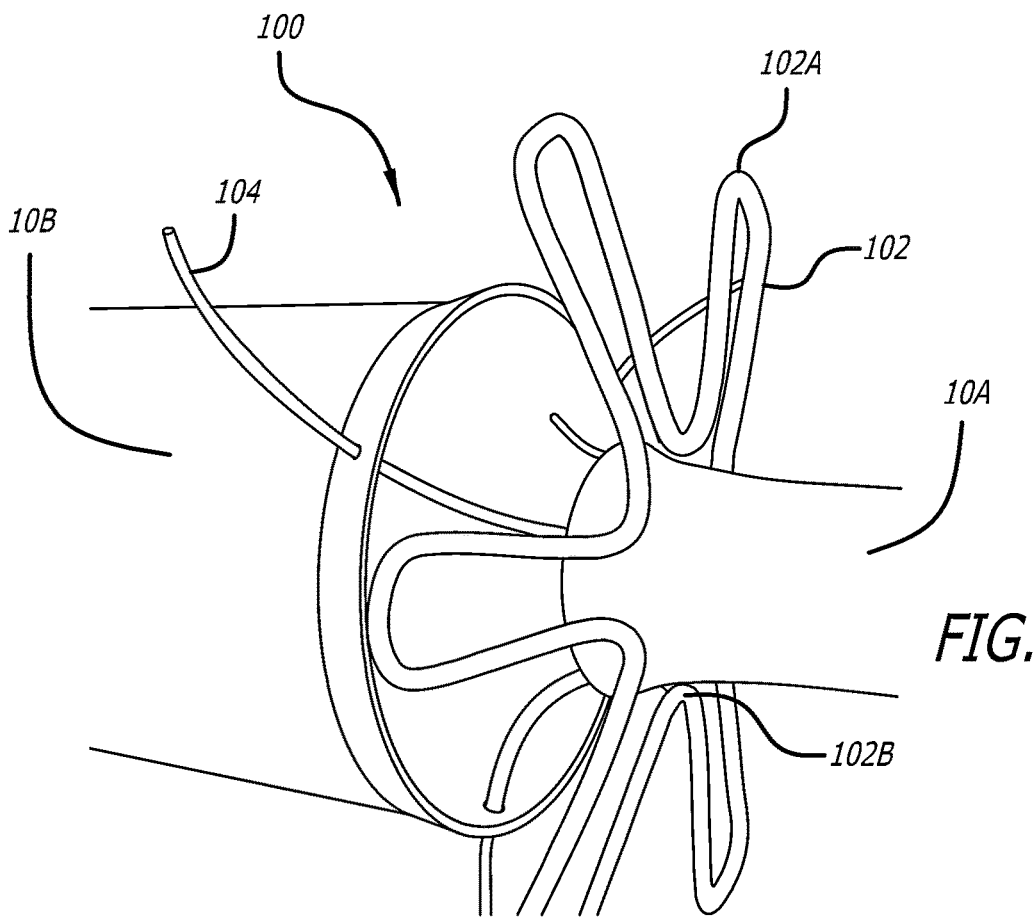
FIG. 16 illustrates the device of FIG. 1 connecting two tubular structures.

Referring to FIG. 15, the distal ends of the elongated pins 104 are positioned into the opening of the second vessel 10B. Once inside, the peaks 102A of the ring 102 are rotated or pulled radially away from the second vessel 10B, causing the elongated pins 104 to penetrate the tissue of the second vessel 10B, as seen in FIG. 16.

Figure 17:
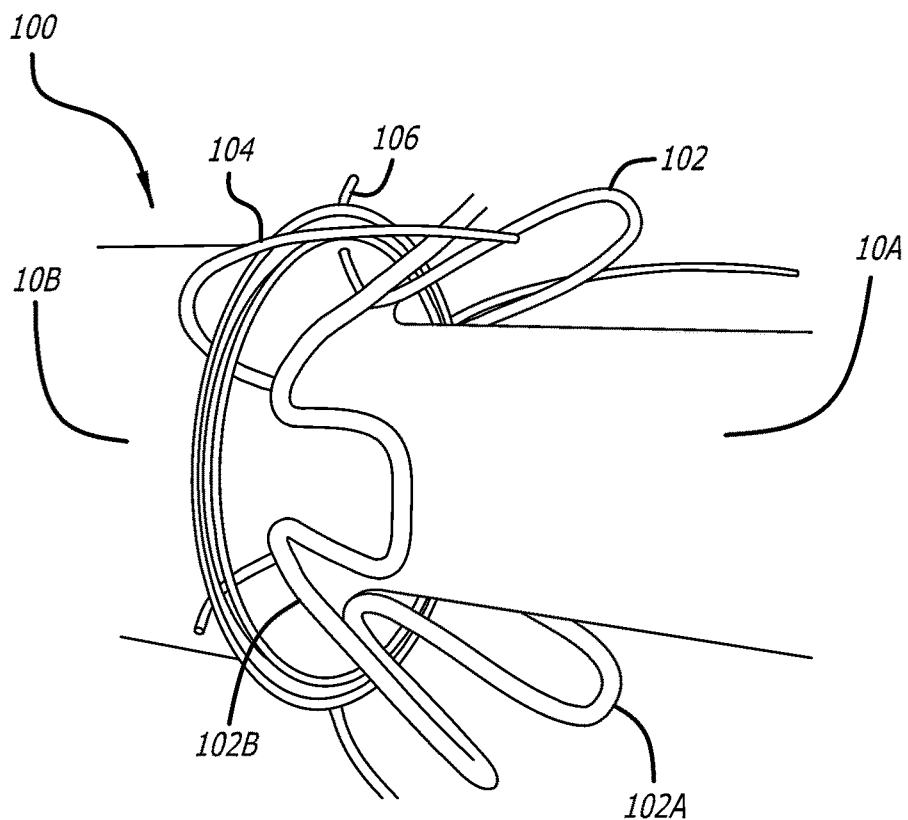
FIG. 17 illustrates the device of FIG. 1 connecting two tubular structures.
Figure 18:
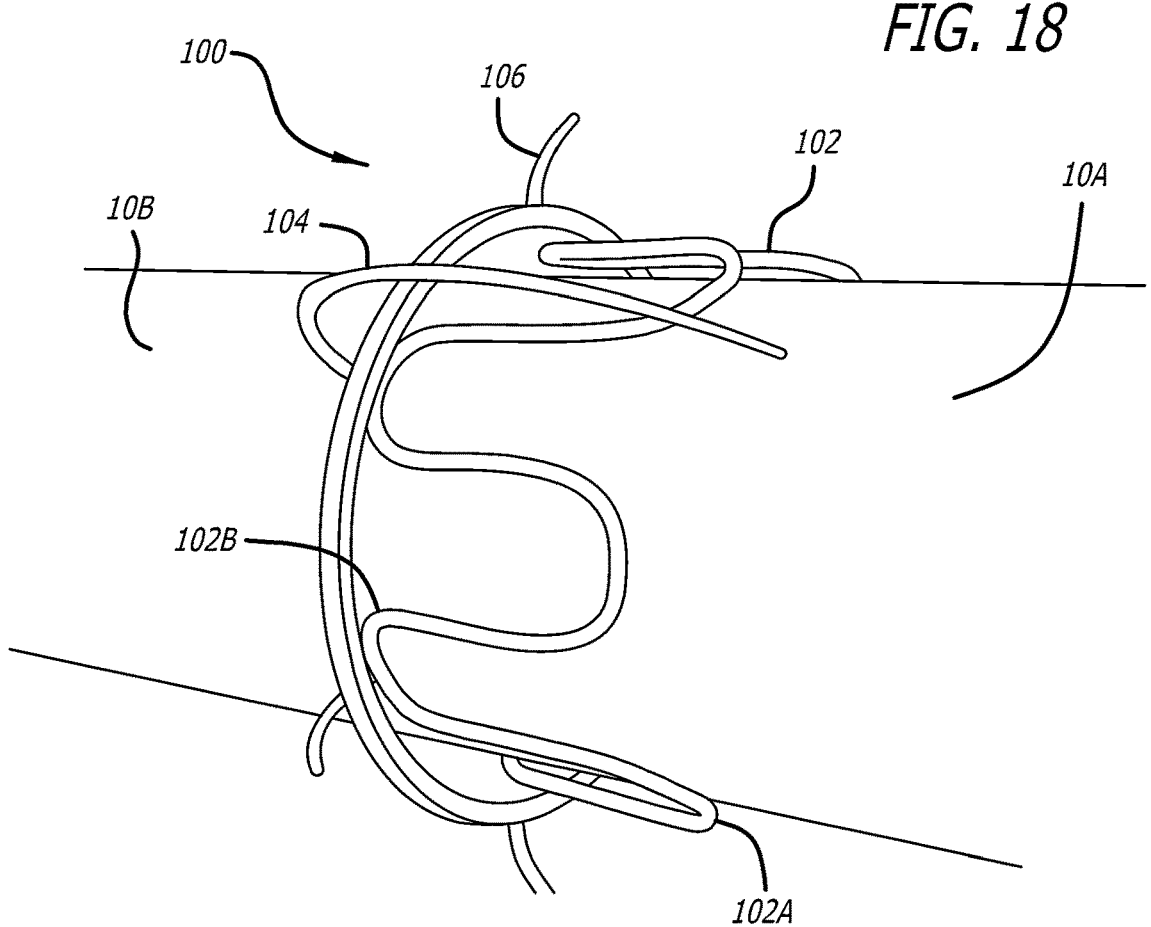
FIG. 18 illustrates the device of FIG. 1 connecting two tubular structures.
Figure 19:
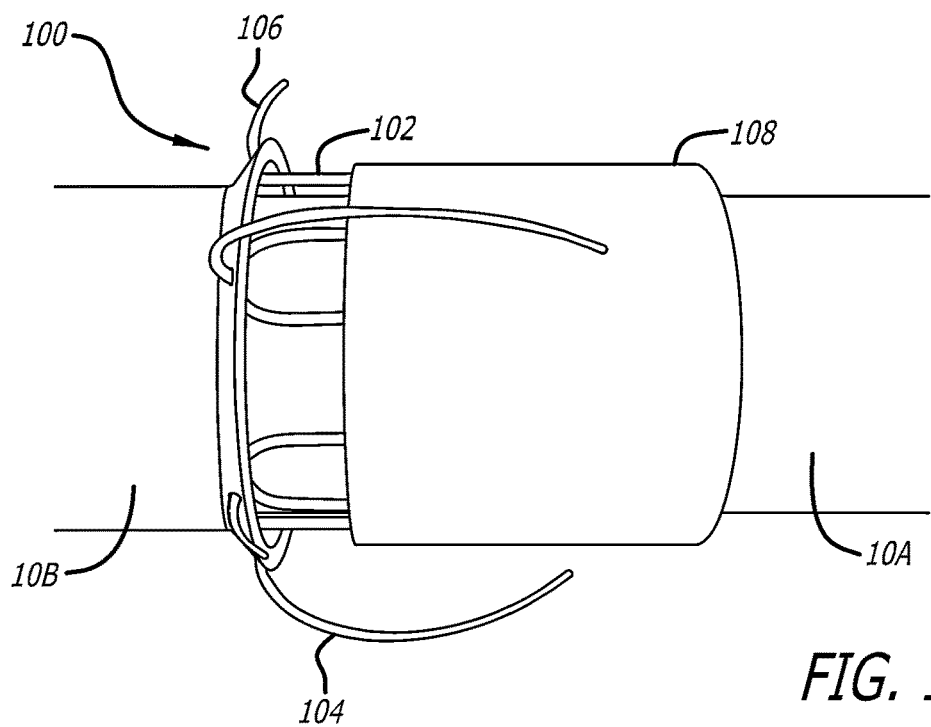
FIG. 19 illustrates the device of FIG. 1 connecting two tubular structures.
Figure 20:
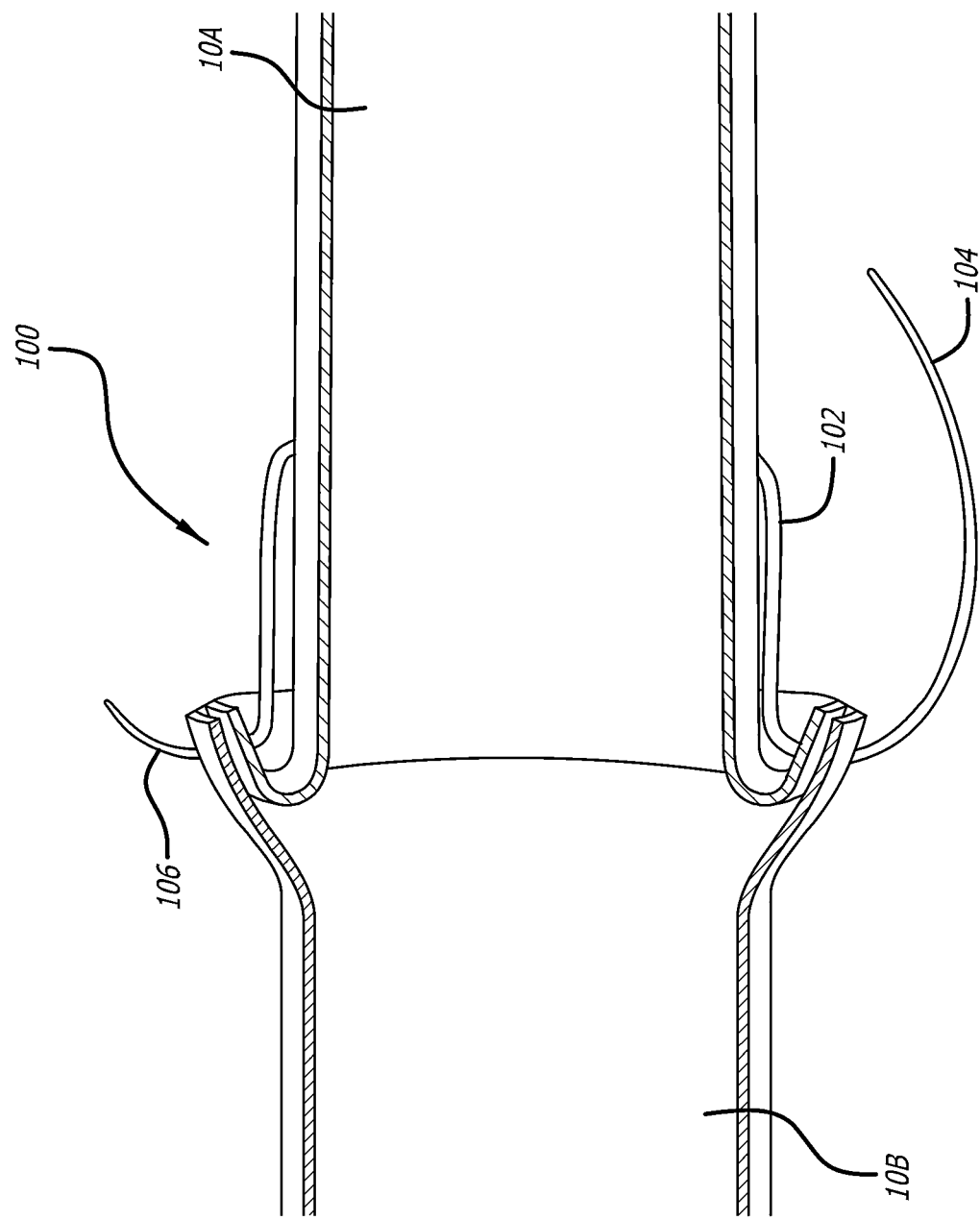
FIG. 20 illustrates the device of FIG. 1 connecting two tubular structures.

Turning to FIG. 17, as the waves of the ring 102 are further rotated towards the outside of the first vessel 10A, the smaller pins 106 also pass through the tissue of the second vessel 10B. As shown in FIG. 18, once the eversion has completed, the waves of the ring 102 are circumferentially positioned around the outside of the first vessel 10A, the smaller pins 104 are angled radially outward, and the elongated pins 104 extend away from the second vessel 10B. If the retaining band 108 is used, it can then be slid over the waves of the ring 102 to help maintain the everted configuration of the device 100, as seen in FIG. 19. FIG. 20 illustrates a cross sectional view of the device 100 in the everted configuration.

Figure 21:
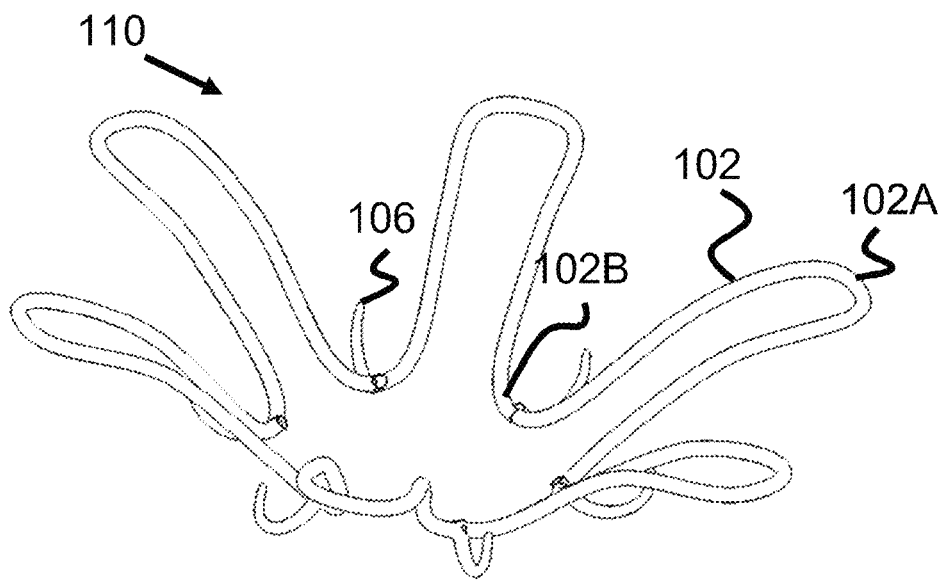
FIG. 21 illustrates a perspective view of a tubular connection device according to the present invention.
Figure 22:
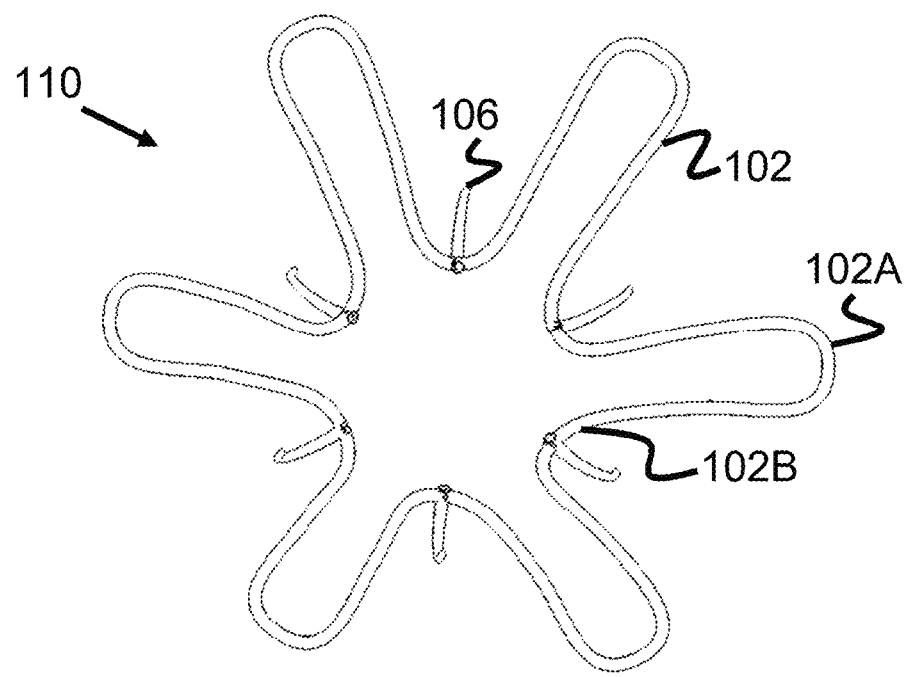
FIG. 22 illustrates a perspective view of a tubular connection device according to the present invention.

FIGS. 21 and 22 illustrate another embodiment of a device 110 that is generally similar to the previously described device 100. However, the device 110 only includes a plurality of smaller pins 106 extending from the troughs 102B of the wave shapes of the ring 102. The device 110 is shown in the Figures in its fully everted configuration, such that the pins 106 are positioned radially outward and curved upward. Unlike the prior device 100, the device 110 may require a smaller range of eversion, depending on its use. For example, the waves of the ring 102 may evert or move from about 0 degrees (i.e., a generally planar shape) to about 45 degrees (generally concave shape). Use of the smaller, more curved pins 106 and more limited range of eversion may be helpful when connecting the end of one tubular structure to a side opening of another tubular structure, as discussed later in this specification. The ring may be asymmetrical or oval in shape to allow for an elongated connection between the tubular structures. In an alternate embodiment, the device 110 may remain in a fixed configuration without everting, but the ring 102 provides enough flexibility such that the pins 106 can be curved back individually to engage the tissues one at a time.

Figure 23:
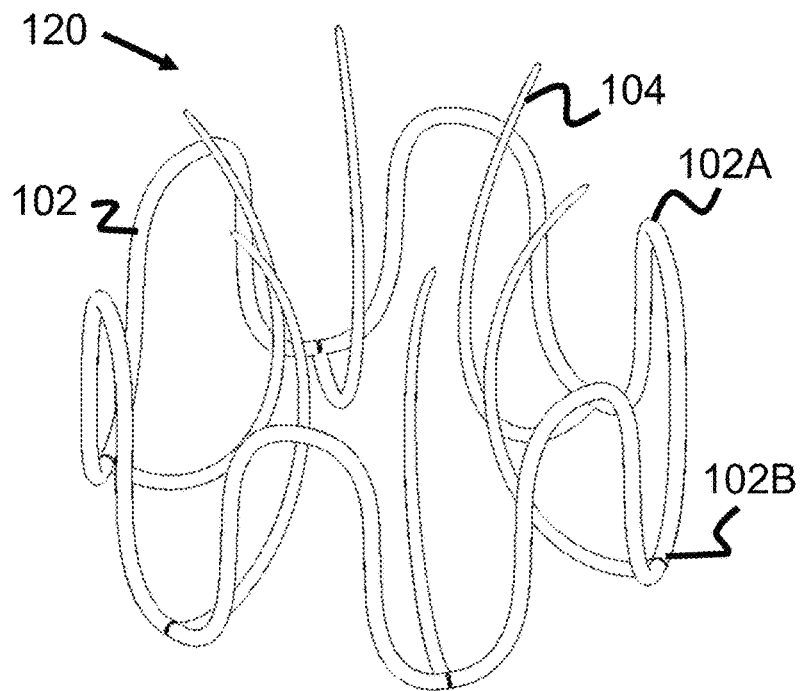
FIG. 23 illustrates a perspective view of a tubular connection device according to the present invention.
Figure 24:
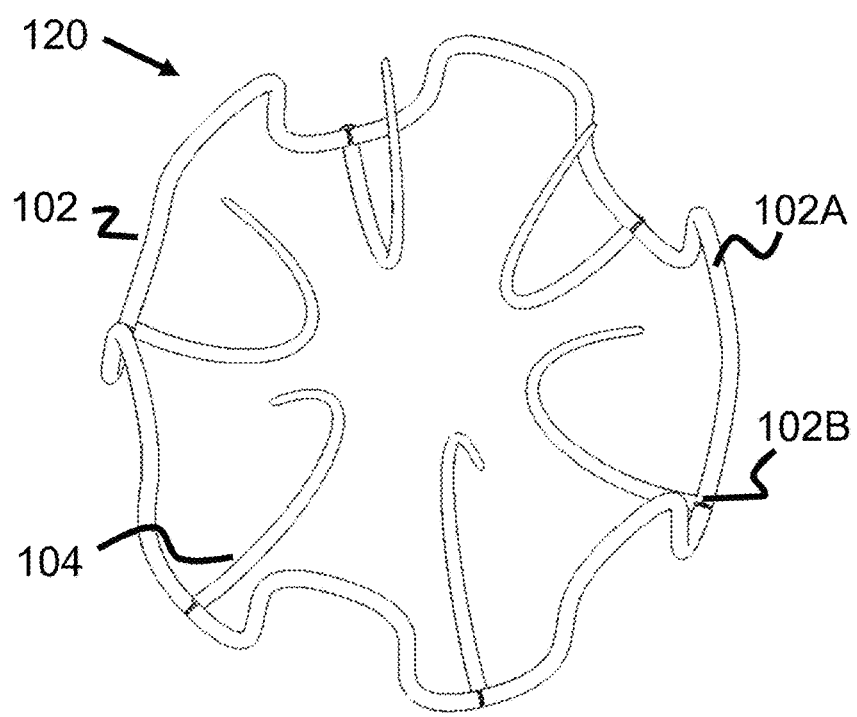
FIG. 24 illustrates a perspective view of a tubular connection device according to the present invention.
Figure 25:
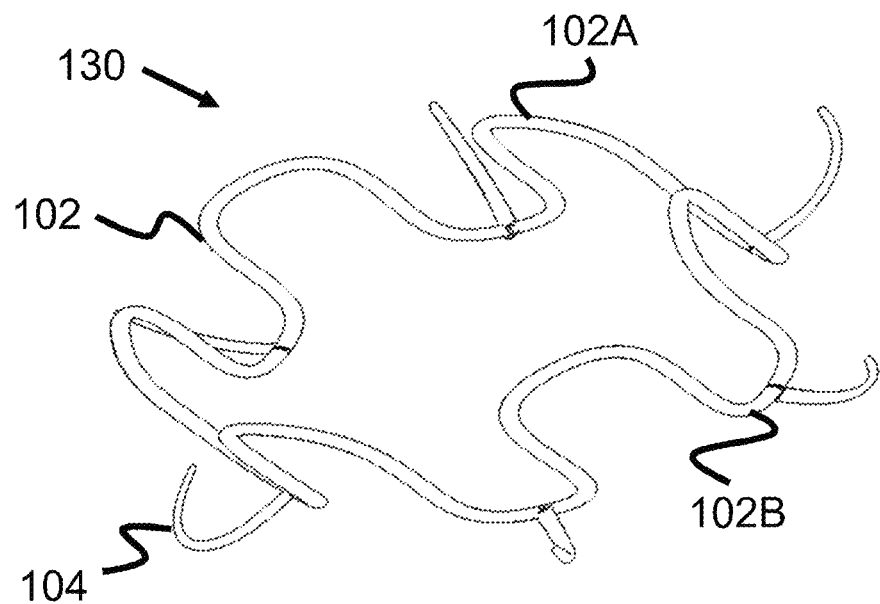
FIG. 25 illustrates a deployment device for a tubular connection device according to the present invention.
Figure 26:
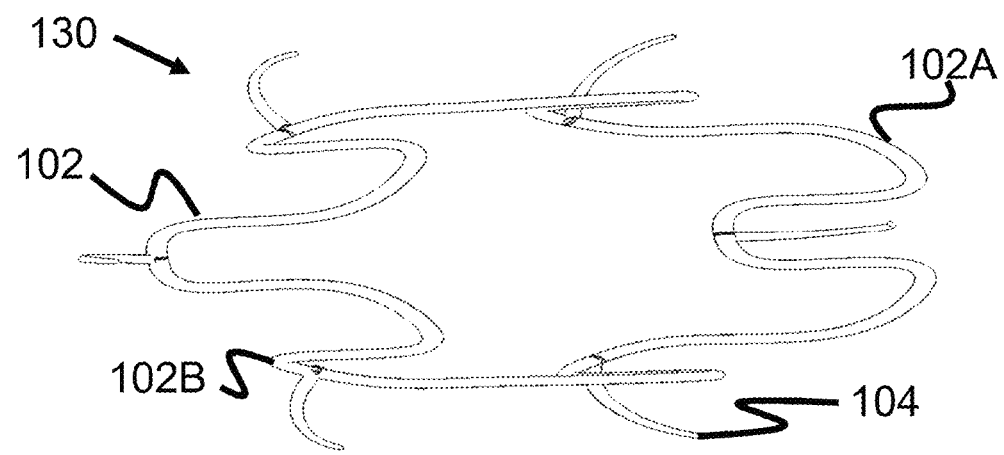
FIG. 26 illustrates a deployment device for a tubular connection device according to the present invention.
Figure 27:
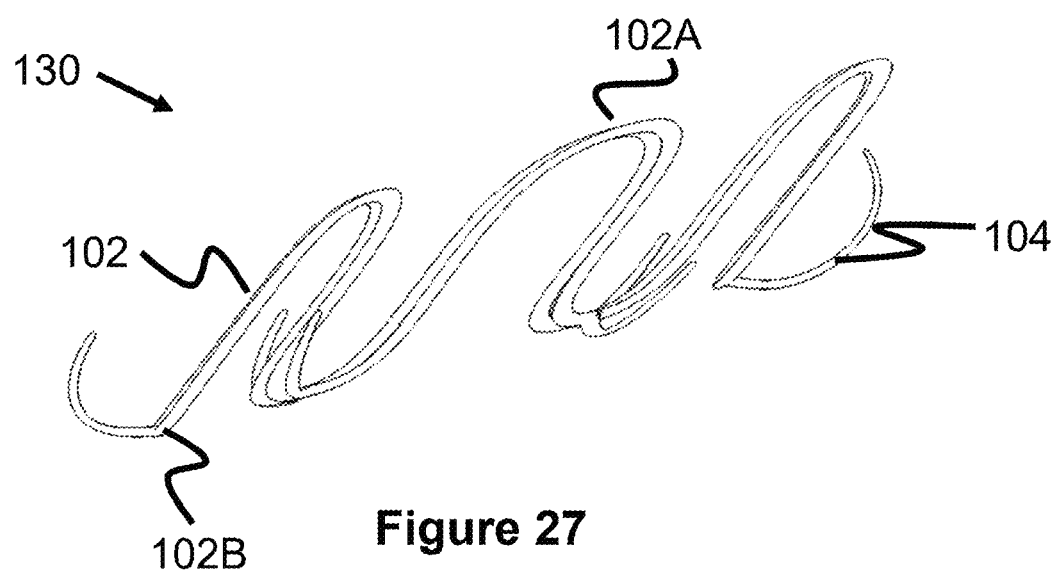
FIG. 27 illustrates a deployment device for a tubular connection device according to the present invention.
Figure 28:
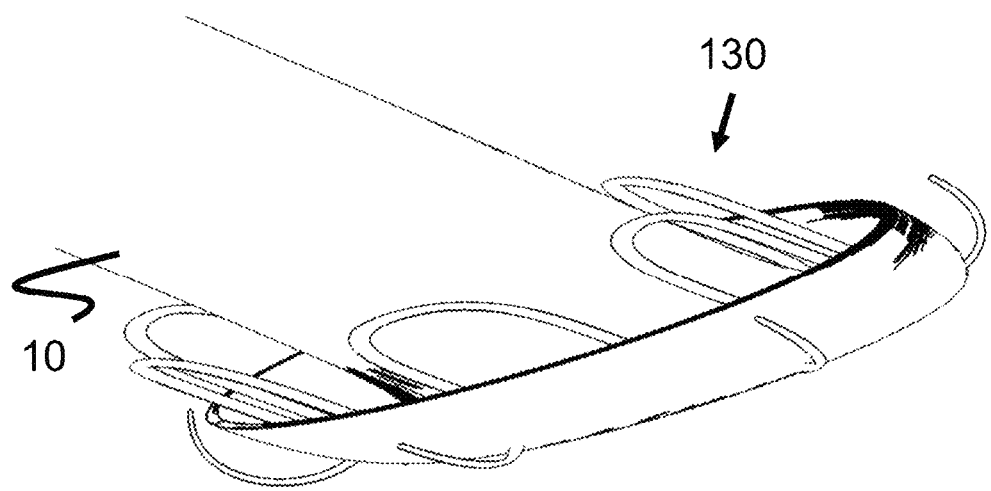
FIG. 28 illustrates a deployment device for a tubular connection device according to the present invention.
Figure 29:
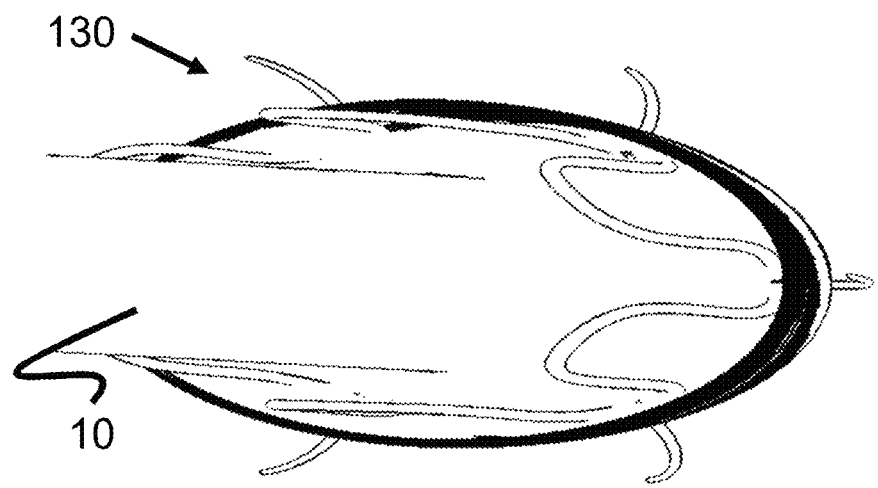
FIG. 29 illustrates a deployment device for a tubular connection device according to the present invention.

FIGS. 23 and 24 illustrate another embodiment of a device 120 that is generally similar to the previously described device 100. However, the device 120 only includes longer pins 104 extending from each of its troughs 102B. The device 120 otherwise everts in a manner similar to that described for device 100. Use of only the longer pins 104 may be particularly useful when connecting a tubular structure to a cavity, such as a bladder, as described later in this specification.

FIGS. 25-29 illustrate another embodiment of a device 130 that is generally similar to the previously described device 120, but has an angled, oval shape. As seen best in FIG. 26, the ring 102 forms a generally oval shape when viewed from above or below, and as seen best in FIG. 27, the waves of the ring are "slanted" or angled in a non-perpendicular direction relative to the overall plane of the ring 102. This oval, angled shape can be helpful when connecting two structures that intersect at a non-perpendicular angle relative to each other.

Figure 30:
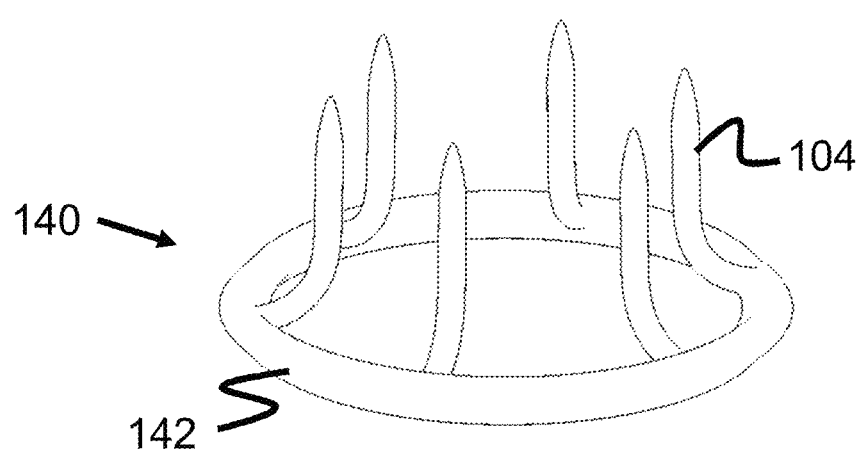
FIG. 30 illustrates a deployment device for a tubular connection device according to the present invention.
Figure 31:
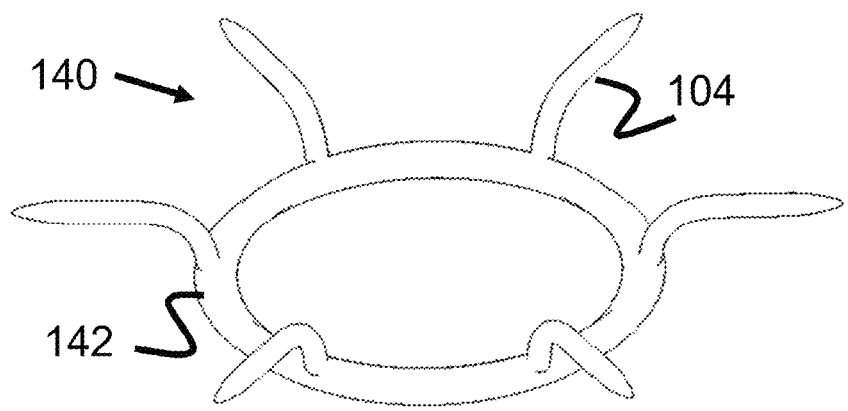
FIG. 31 illustrates a deployment device for a tubular connection device according to the present invention.
Figure 32:
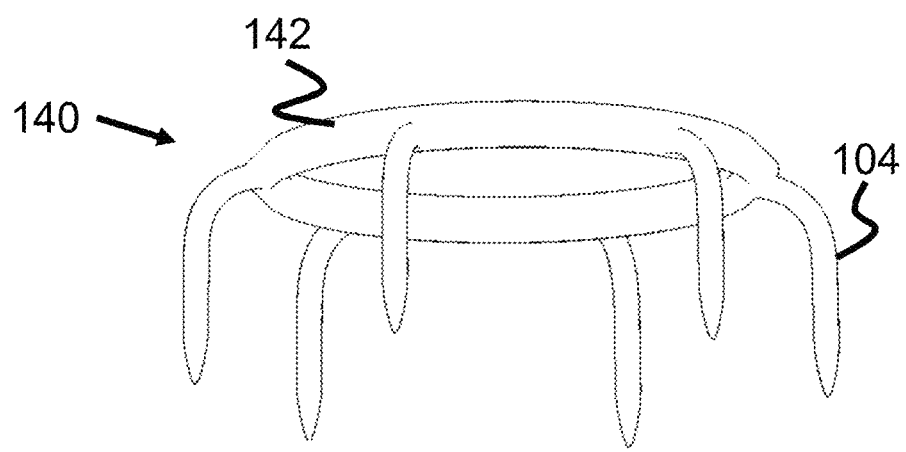
FIG. 32 illustrates a deployment device for a tubular connection device according to the present invention.

FIGS. 30-32 illustrate another embodiment of a device 140 that is generally similar to the previously described embodiments of this specification, but instead of a wave-shaped ring, the device 140 includes a ring 142 composed of flexible material, such as silicone, rubber, latex, or other elastomeric materials. The pins 104 may be composed of more rigid materials such as metal or polymers, and can be connected to the ring 142 with a variety of techniques, such as being mechanically engaged with the ring 142 or connected via adhesive. FIG. 30 illustrates the device 140 in a normal or inverted configuration with the pins 104 curved radially inwards, FIG. 31 illustrates the device 140 in a partially everted configuration with the pins 104 pointed radially outward from the center of the device 140, and FIG. 32 illustrates the device 140 in a fully everted configuration with the pins 104 curving radially outward from the device 140. In this respect, the device 140 can be used in a similar manner as any of the other embodiments of this specification.

In one example delivery method, the devices of the present invention can be deployed with the same instruments used to perform a sutured anastomosis. For example, a surgeon may use these instruments to advance the pins through the tissue and then apply outwardly radial pressure on the ring 102 so as to cause it to evert.

Figure 33:
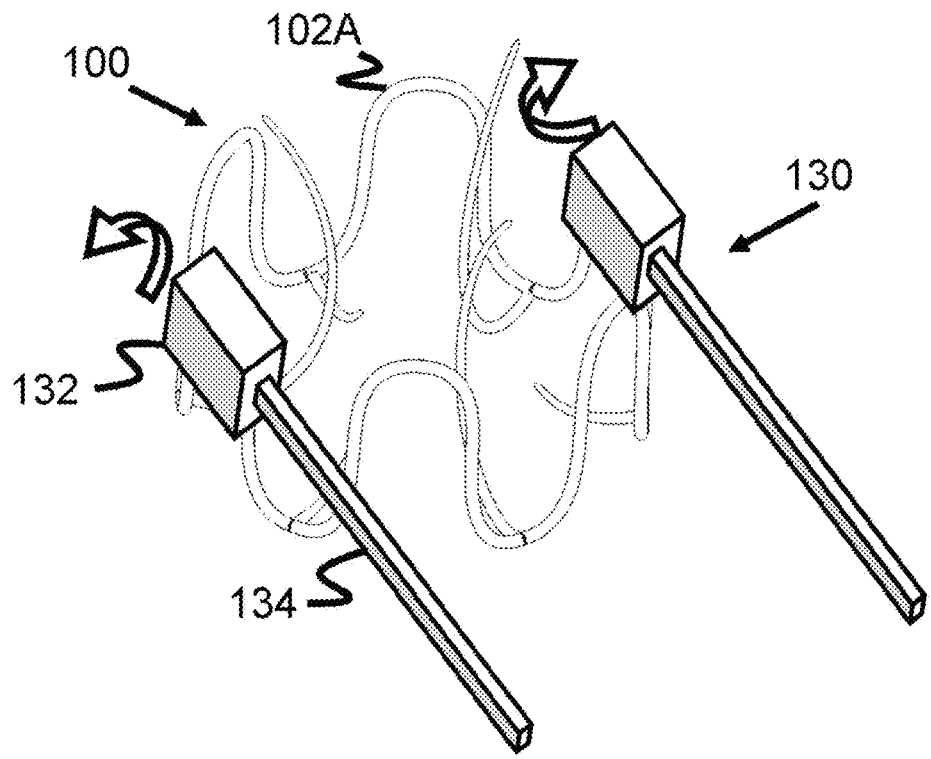
FIG. 33 illustrates a deployment device for a tubular connection device according to the present invention.

In another example delivery method, a deployment device can be used to deploy the devices of the present invention. For example, FIG. 33 illustrates a deployment device 130, comprising to elongated members 134 that are each connected to an engagement portion 132 that is configured to engage a peak 102A of the ring 102. In one example, the engagement portion 132 is a rigid sleeve that is sized and shaped to fit over a portion of the peak 102A. Alternately, other engagement mechanisms are also possible, such as hooks or clamps. Once engaged, the elongated members 134 can be rotated (e.g., via handles) to cause eversion of the device 100. Other deployment devices may be used to hold the device in a particular shape or state of inversion or eversion.

Figure 34:
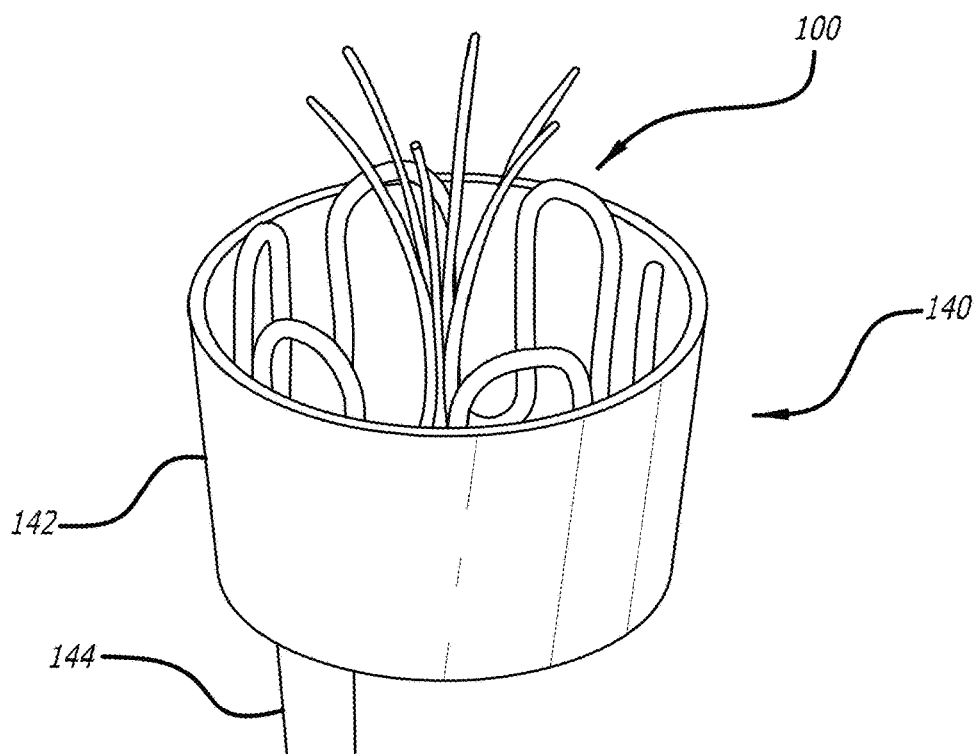
FIG. 34 illustrates a deployment device for a tubular connection device according to the present invention.
Figure 35:
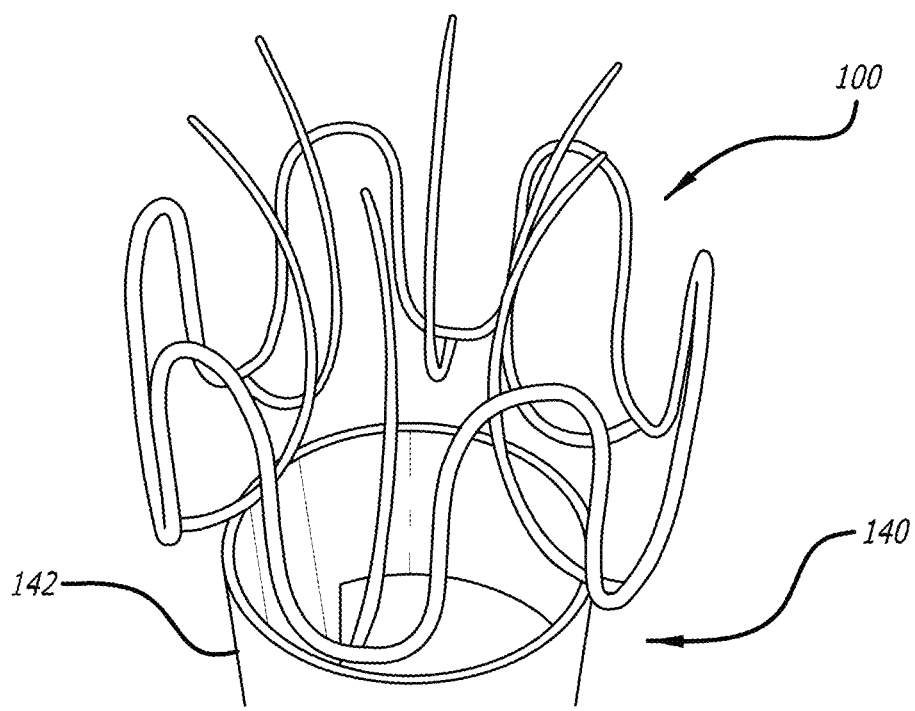
FIG. 35 illustrates a deployment device for a tubular connection device according to the present invention.

In another example delivery method, a deployment device 140 can be used to deploy the device 100 from a compressed configuration, as seen in FIG. 34. The deployment device 140 may include a tubular portion 142 in which the device 100 is compressed within, and an elongated portion 144 that is proximally attached to the tubular portion 142. Optionally, a further device can be used to advance the device 100 out of the tubular portion 142 at a desired location, as seen in FIG. 35.

Figure 36:
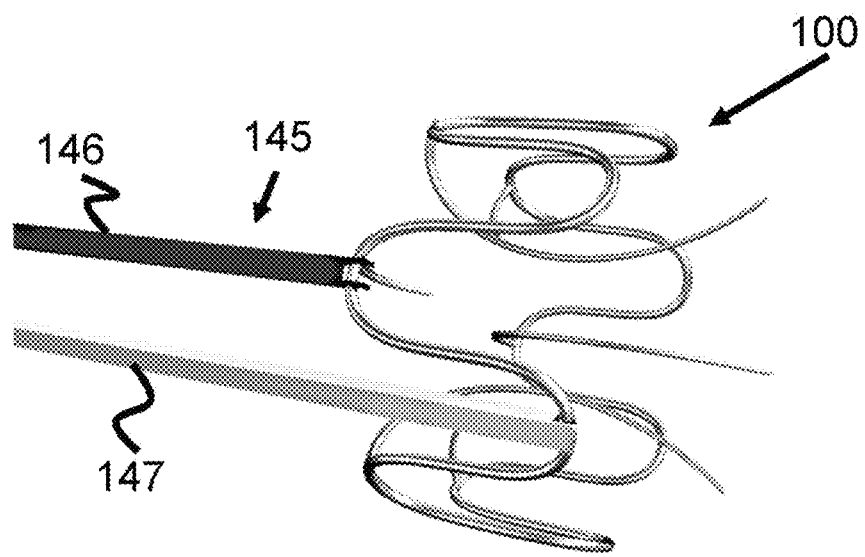
FIG. 36 illustrates a deployment device for a tubular connection device according to the present invention.
Figure 37:
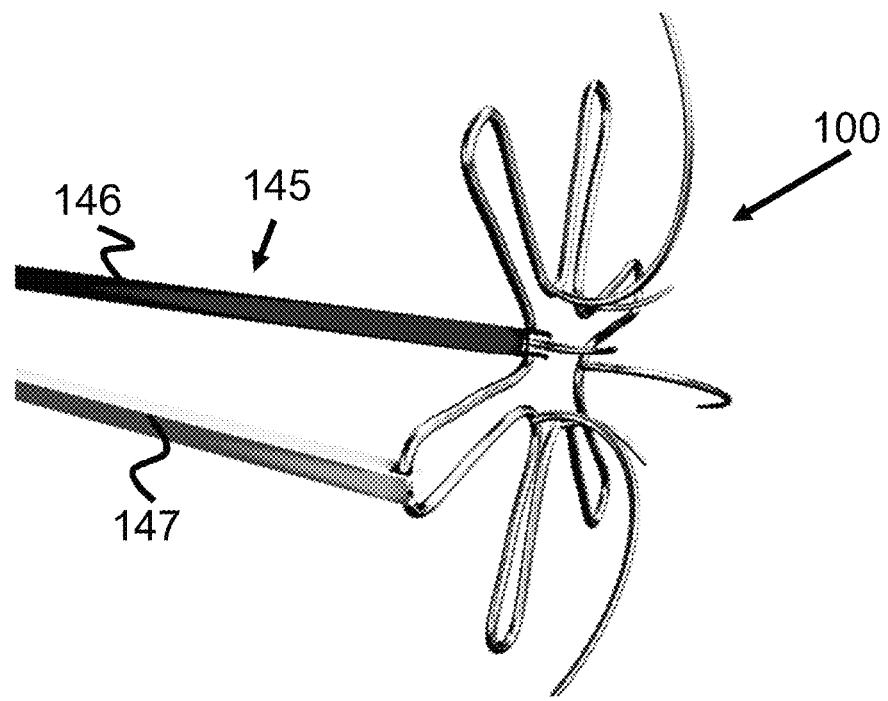
FIG. 37 illustrates a deployment device for a tubular connection device according to the present invention.
Figure 38:
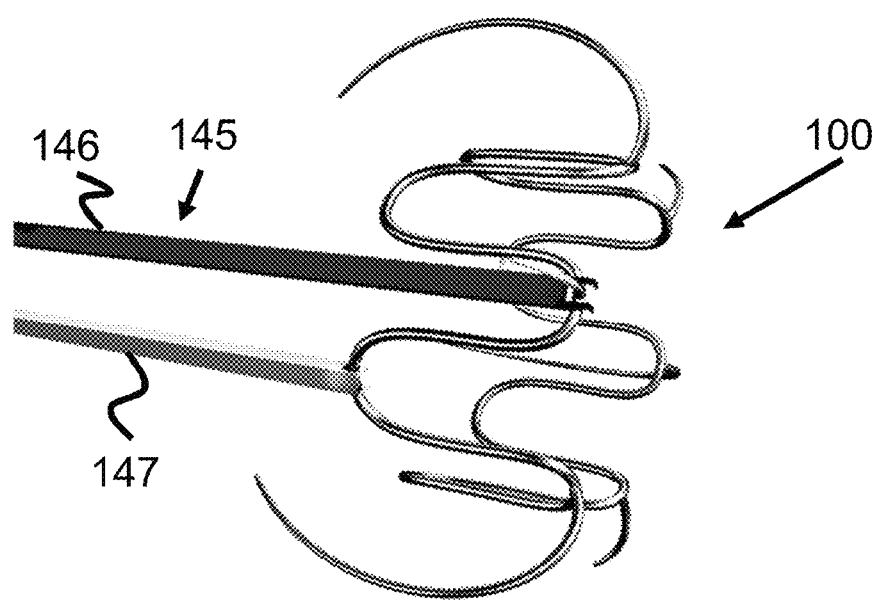
FIG. 38 illustrates a deployment device for a tubular connection device according to the present invention.

FIGS. 36-38 illustrate another example of a delivery/deployment device 145 and method of using the same. The device comprises two elongated arm members 146 and 147, each of which having distal ends that engage the ring of the device 100. For example, the distal ends of the arms 146/147 may form a groove or form right-angle fingers that removably engage the ring of the device 100. Unlike the device 130 which engages the device with its arms 134 in a perpendicular orientation, the device 145 allows the arms 146/147 to engage the device 100 from a parallel or longitudinal orientation. Preferably, one arm 146 can be engaged with a more proximal location on the device 100 (e.g., a trough of the ring) and the other arm 147 can be engaged with a more distal location on the device 100 (e.g., a peak of the ring), thereby allow the user to push one arm and pull the other arm to cause eversion of the device 100.

Figure 39:
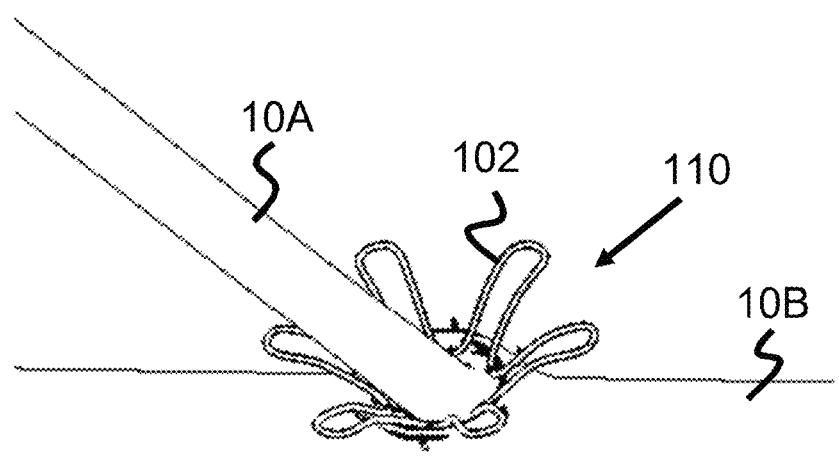
FIG. 39 illustrates a perspective view of a tubular connection device according to the present invention.
Figure 40:
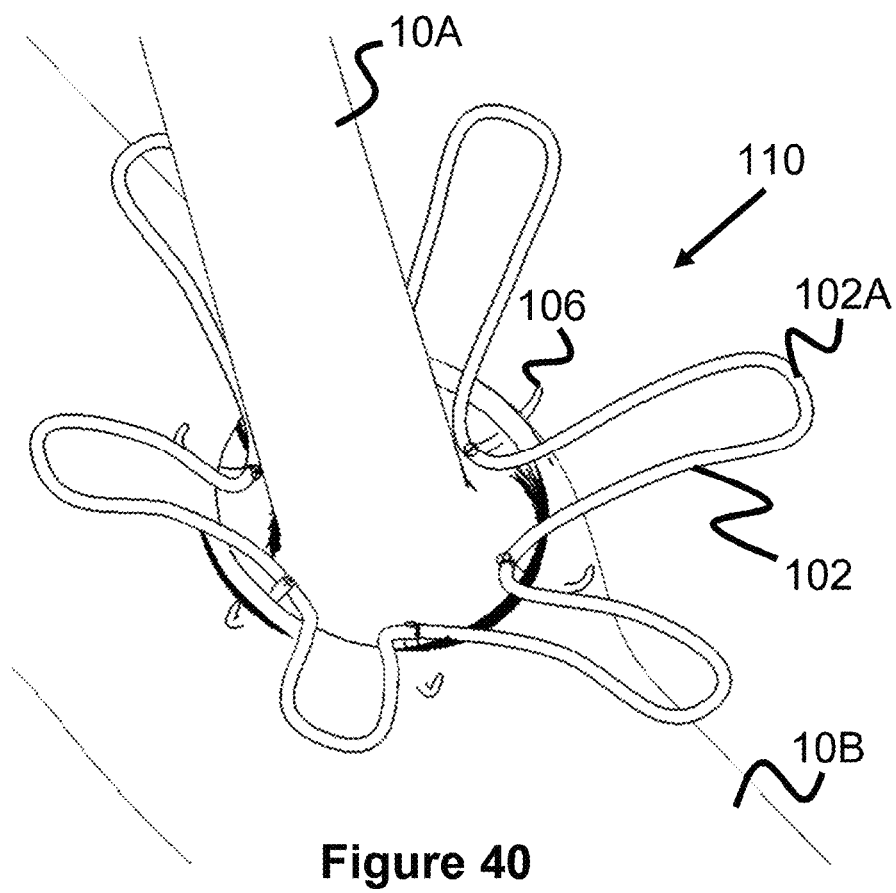
FIG. 40 illustrates a perspective view of a tubular connection device according to the present invention.

While FIGS. 13-20 illustrate a method of attaching two ends of two tubular structures together with a device 100, connections between differently-shaped structures are also possible. For example, FIGS. 39 and 40 illustrate an end of a first blood vessel 10A being connected to a side opening of a second blood vessel 10B with device 110. Initially, peaks 102A of the ring 102 of the device 110 are positioned so the device 110 is in a generally planar position, allowing the ends of the smaller pins 106 to be angled somewhat downward or in a direction aligned with the longitudinal axis of the vessel 10A. The outside of the tissue around the end of the opening of the vessel 10A is place over the ends of the pins 106 such that the pins 106 penetrate through the tissue. Next, the ends of the pins 106 and the end of the first vessel 10A are placed into the aperture of the second vessel 10B. Finally, the ring 102 is rotated towards the first vessel 10A, causing the pins 106 to also penetrate the tissue surrounding the opening of the second vessel 10B, as seen in FIG. 40.

Figure 41:
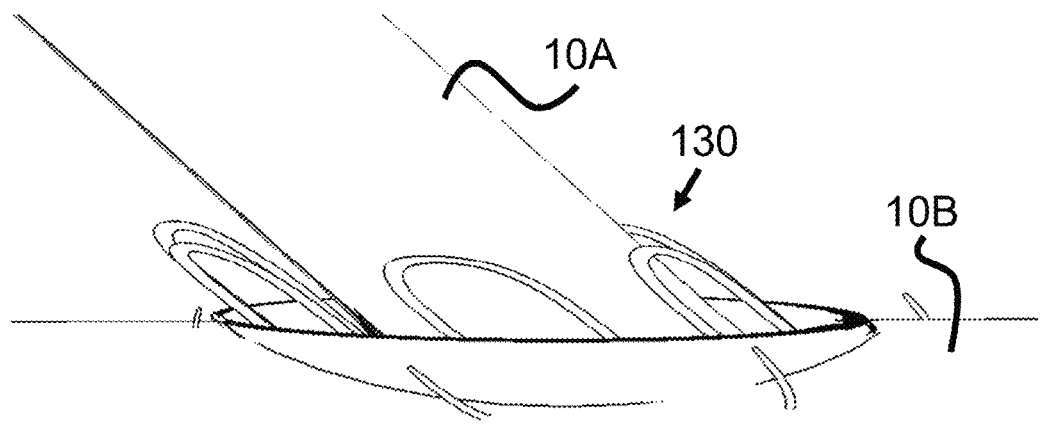
FIG. 41 illustrates a deployment device for a tubular connection device according to the present invention.

A similar procedure can be performed with the oval/angled device 130, as seen in FIG. 41. Additionally, the device 130 is first rotated to align its angled ring 102 between the first vessel 10A that will intersect the second vessel 10B at a non-perpendicular angle. The remaining steps are similar to those previously described for prior embodiment.

Figure 42:
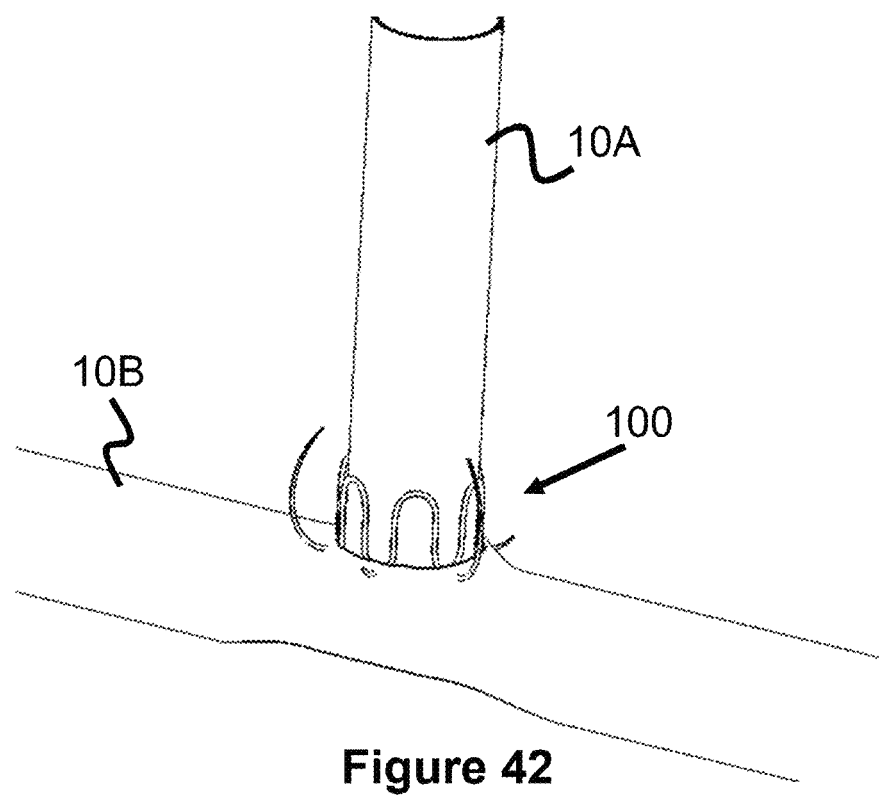
FIG. 42 illustrates a perspective view of a tubular connection device according to the present invention.
Figure 43:
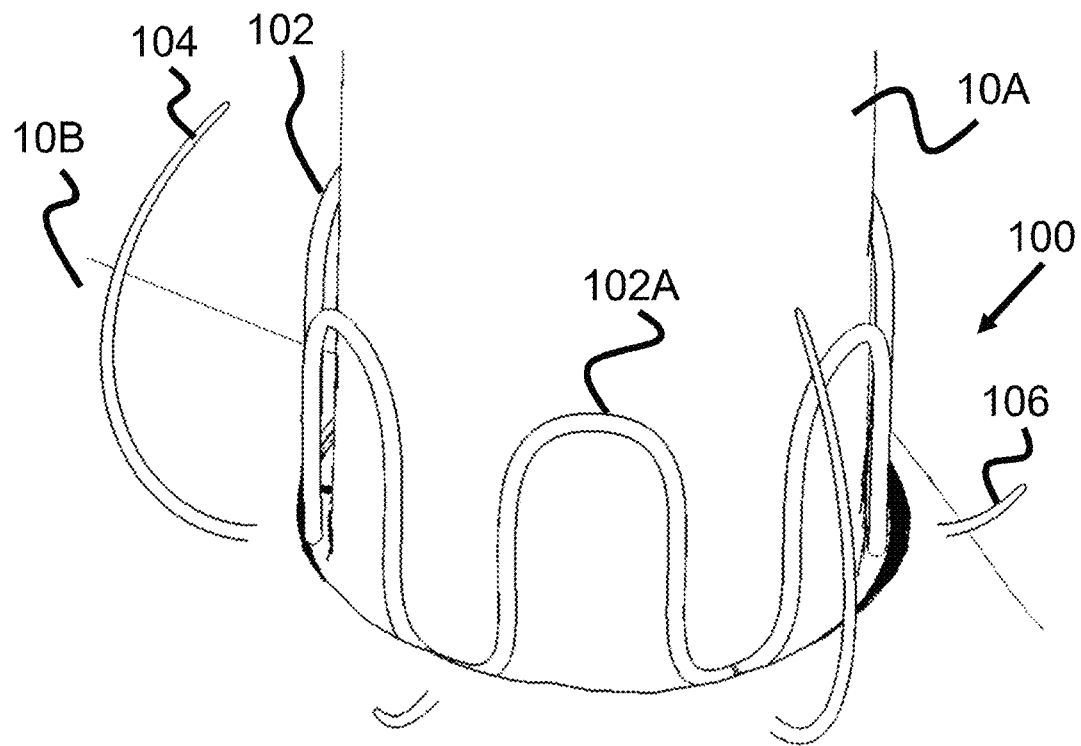
FIG. 43 illustrates a perspective view of a tubular connection device according to the present invention.

FIGS. 42 and 43 illustrate the device 100 being used to connect the end of a first vessel 10A with a side aperture of a second vessel 10B. The connection method is similar to that described for FIGS. 9-15.

Figure 44:
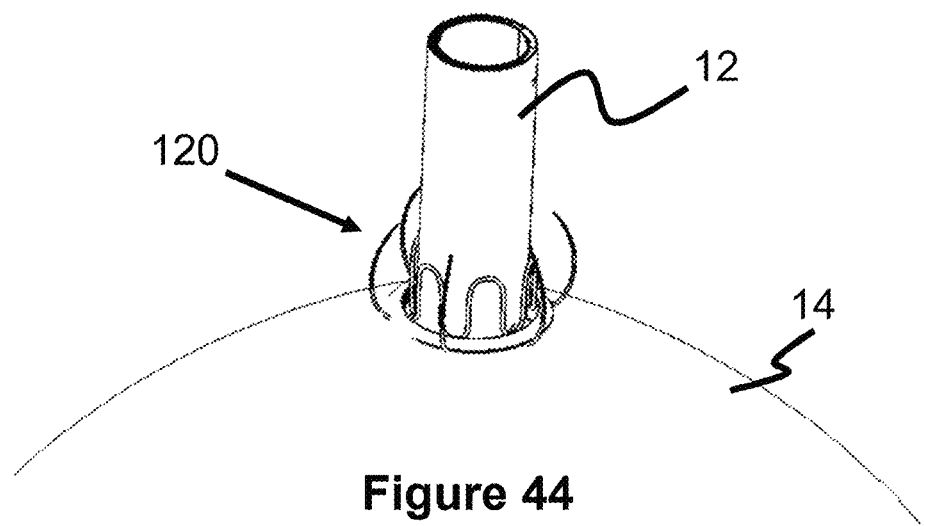
FIG. 44 illustrates a perspective view of a tubular connection device according to the present invention.
Figure 45:
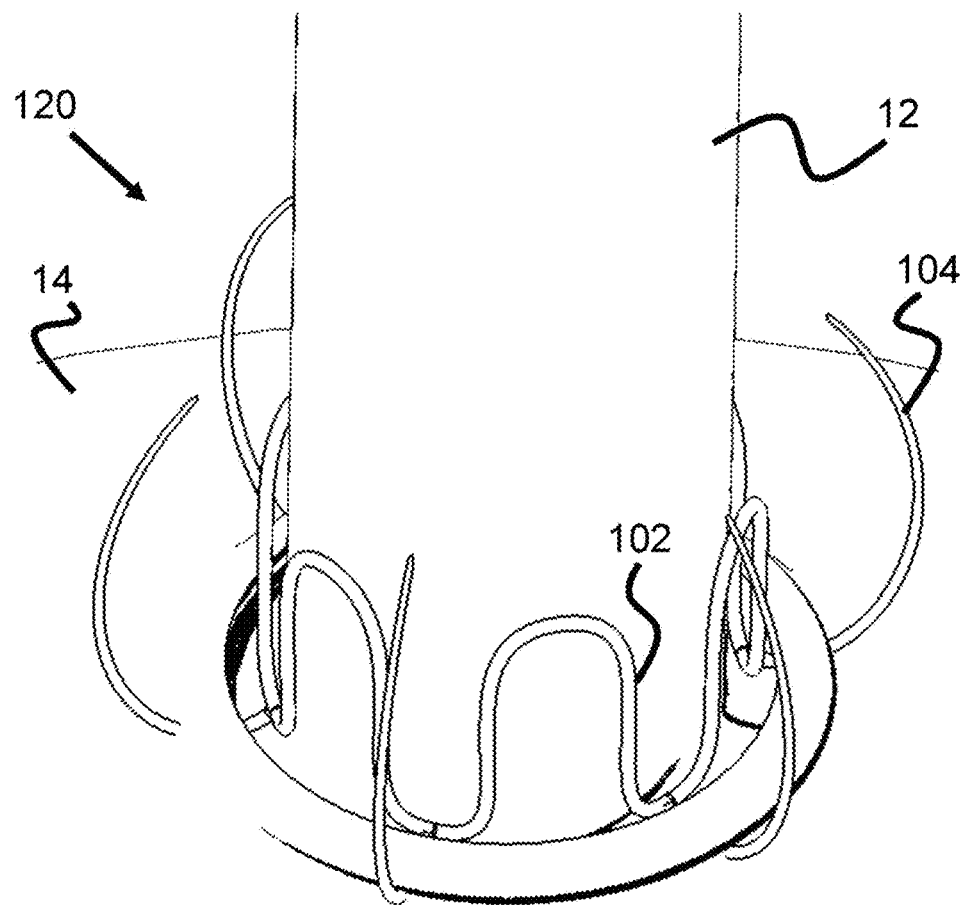
FIG. 45 illustrates a perspective view of a tubular connection device according to the present invention.

FIGS. 44 and 45 illustrate the device 120 being used to connect a bladder 14 with a urethra 12. The connection process proceeds in a manner similar to that described in FIGS. 9-15, except that the device 120 is first placed over and connected to the urethra 12, then the device 120 is passed into the opening of the bladder 14 so that eversion of the ring 102 causes the pins 104 to pierce the bladder tissue. Additionally, the device 120 may be relatively thicker and may have somewhat longer pins than the previously described embodiments. Further, the device 120 may be also be delivered through the urethra during a procedure.

Figure 46:
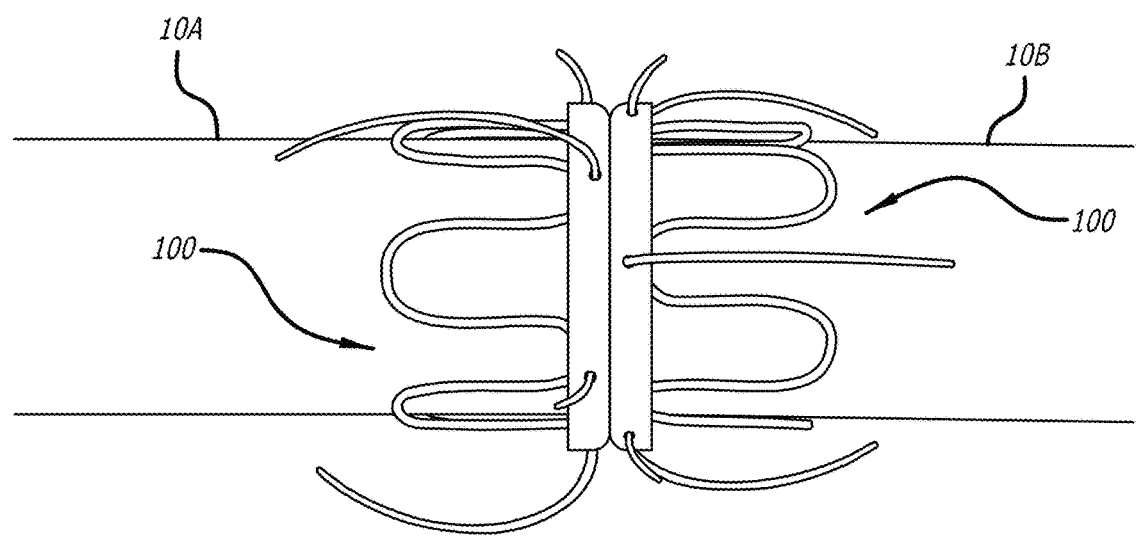
FIG. 46 illustrates use of a deployment device for a tubular connection device according to the present invention.
Figure 47:
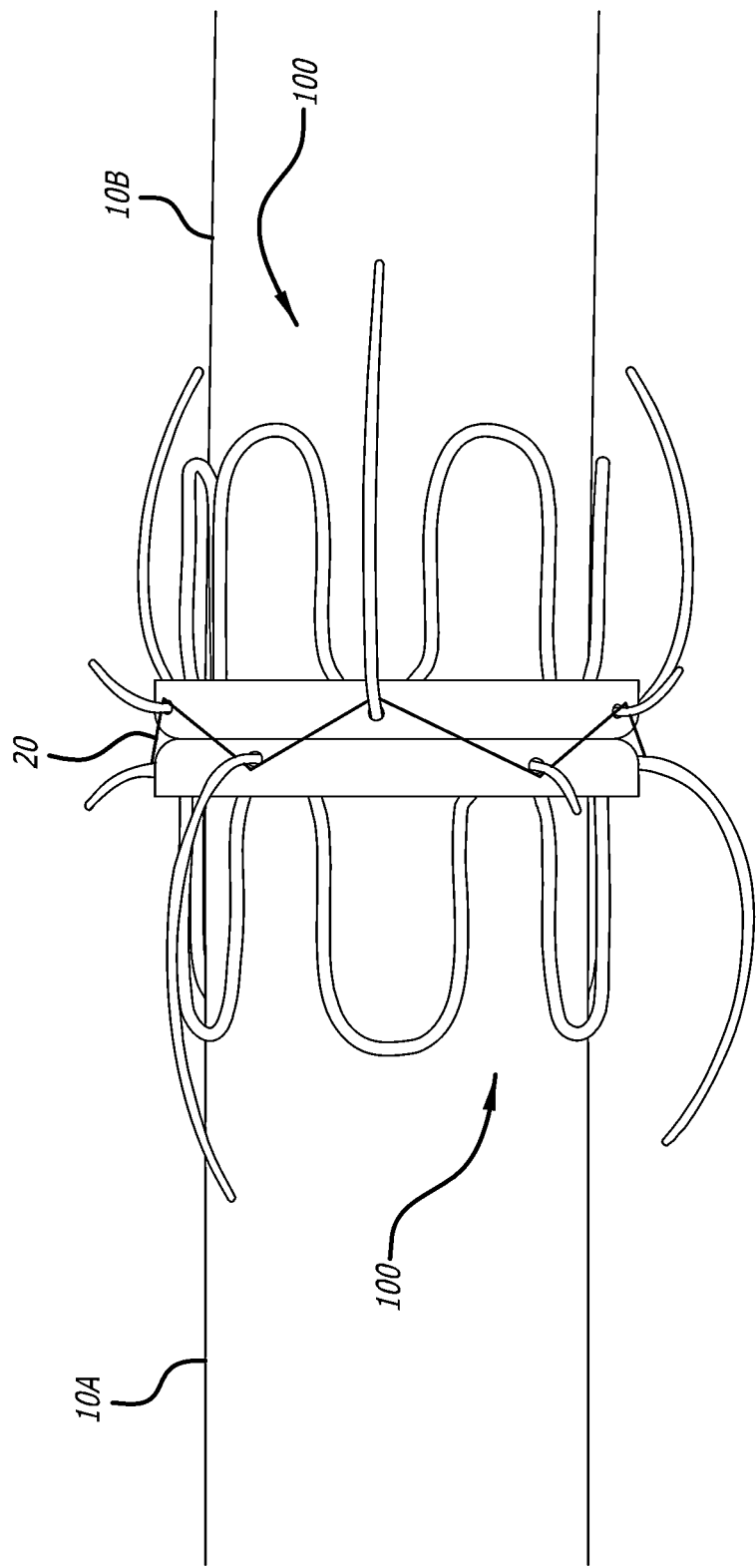
FIG. 47 illustrates use of a deployment device for a tubular connection device according to the present invention.

While the devices of this specification are described as being the primary mechanism of connecting two structures within a patient, they can also be used to prepare one or more ends of a structure for connection via a different mechanism. FIG. 46 illustrates two devices 100 that are each used on a first vessel 10A and a second vessel 10B to invert the tissue at each of their ends. This may allow them to be better or more easily connected via another connection mechanism such as sutures, mechanical connection (e.g., staples), or adhesive. FIG. 47 illustrates one specific connection technique in which suture 20 is woven between/around the pins of both devices (and optionally through the tissue as well).

Figure 48:
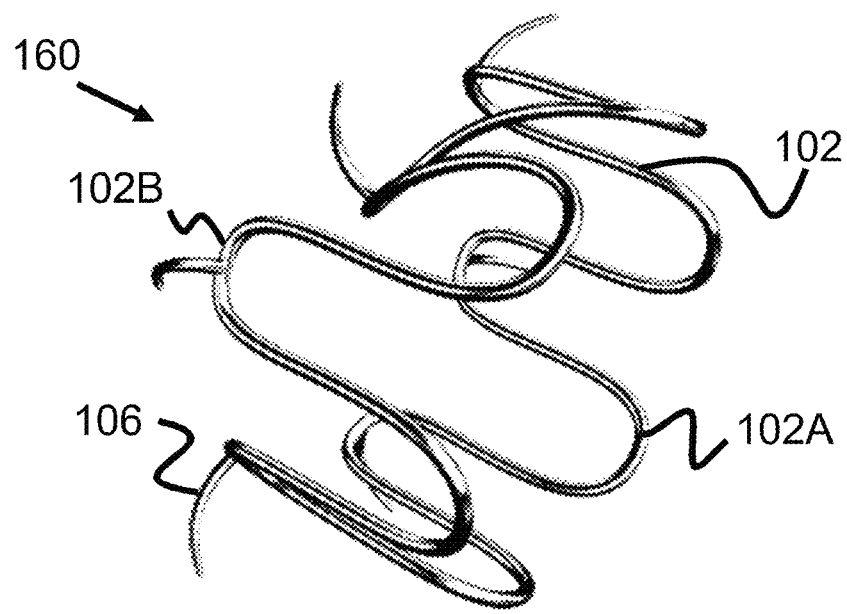
FIG. 48 illustrates a deployment device for a tubular connection device according to the present invention.
Figure 49:
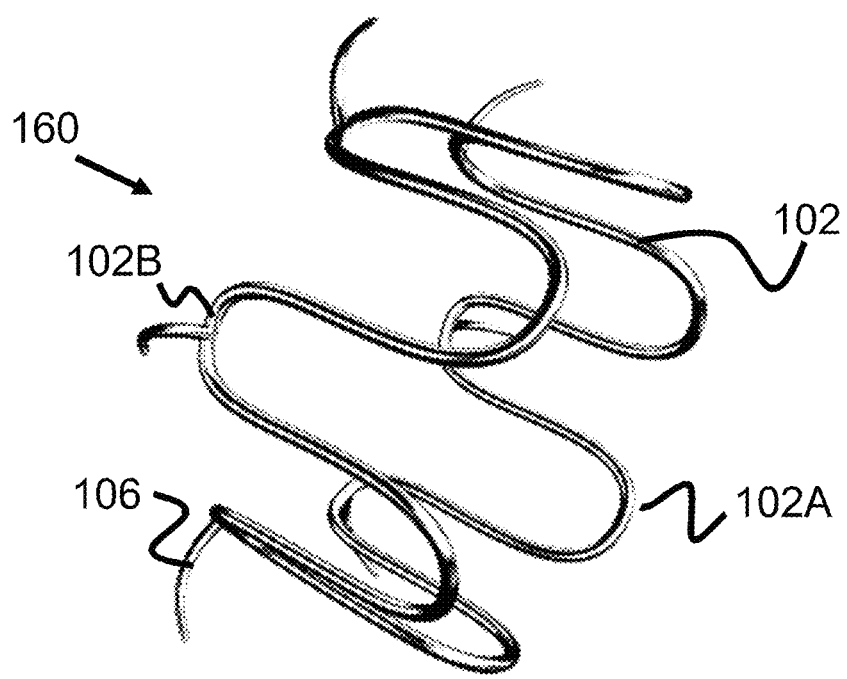
FIG. 49 illustrates a deployment device for a tubular connection device according to the present invention.
Figure 50:
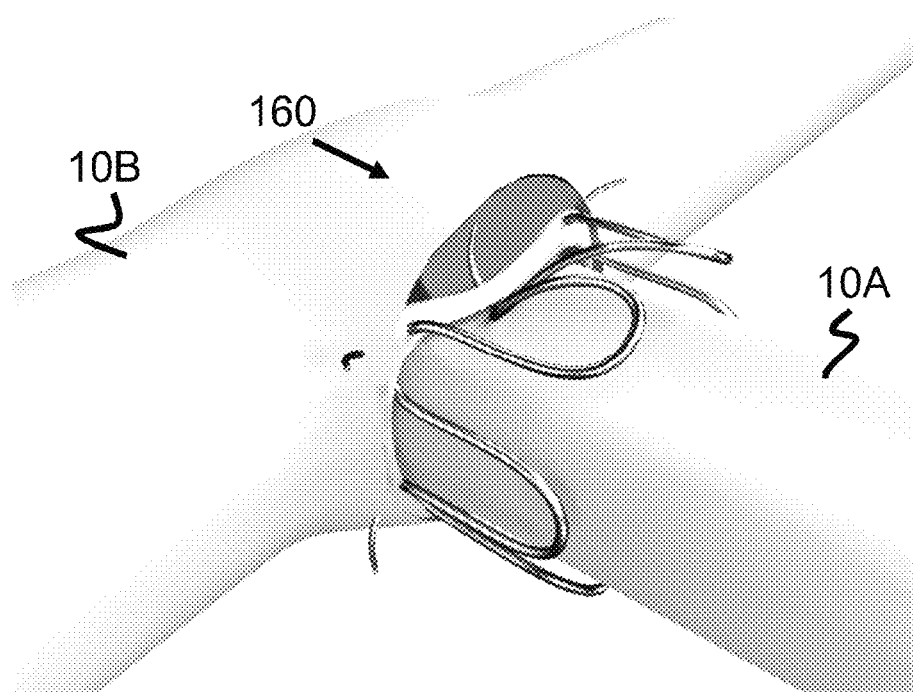
FIG. 50 illustrates a deployment device for a tubular connection device according to the present invention.
Figure 51:
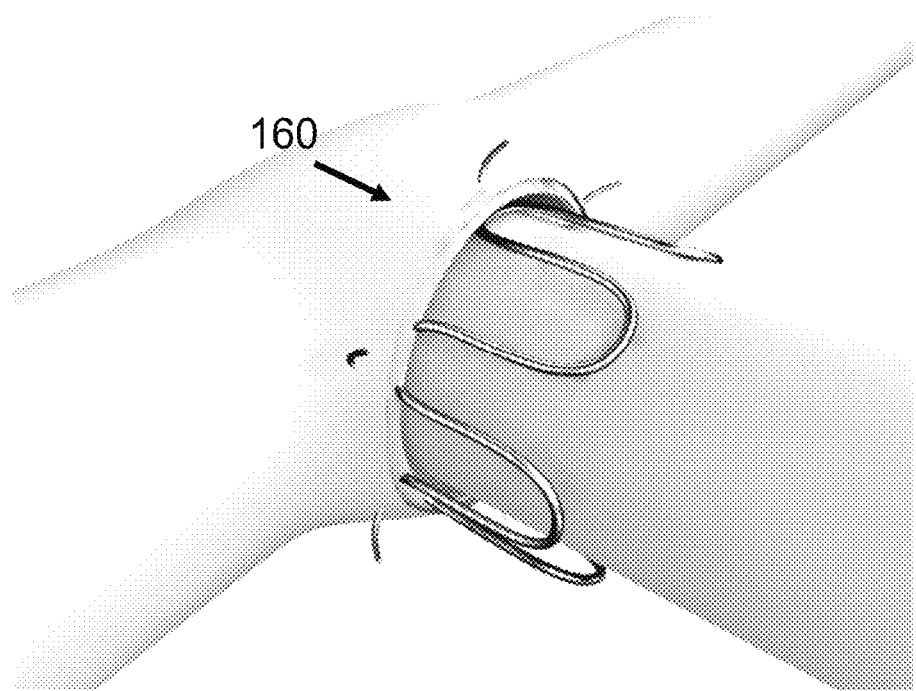
FIG. 51 illustrates a deployment device for a tubular connection device according to the present invention.

While the prior embodiments are discussed as everting or turning inside out to varying degrees, another device and method according to the present invention contemplates only individually bending portions of the device during a procedure. For example, FIGS. 48 and 49 illustrates a device 160 that is generally similar to the previously described devices, having only the smaller pins 106 positioned at the troughs 102B of the ring 102. Unlike previously described methods, the device 160 is delivered within the patient in what would be previously described as an everted configuration, such that the pins 106 are radially, outwardly curved. Instead of everting or inverting the device 160, each "wave" of the ring 102 are bent inwardly (see FIG. 48). to allow one of the pins 106 to pierce a desired tissue location, then released (see FIG. 49). This bending can be performed to connect tissue from two different structures, such as tubular structures 10A and 10B in FIGS. 50 and 51.

It should be understood that the diameter and height of the devices of the present invention may have different sizes, depending on the types of structures that are being connected. For example, if being used to connect blood vessels, the device's diameter may be within a range of 0.2 mm and 45 mm, and its height may be within a range of 0.2 mm and 45 mm. In another example, if being used to connect a bladder and urethra, the device's diameter may be within a range of 5 mm and 25 mm, and its height may be within a range of 5 mm and 25 mm. In another example, if being used to connect portions of an bile duct, fallopian tube, or ureter, the device's diameter may be within a range of 3 mm and 12 mm, and its height may be within a range of 3 mm and 15 mm.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:
1. An anastomosis system, comprising:
   a delivery device, comprising:
      one or more elongated members; and
      one or more engagement portions supported by the one or more elongated members; and
   a treatment device, comprising:
      a ring having a plurality of pins connected to the ring;
      wherein the plurality of pins are configured to insert through tissue of a first and second openings; and, wherein the one or more elongated members move the ring from a first configuration to a second configuration in which the plurality of pins are inside out relative to the first configuration and form a tubular shape to press the tissue of the first and second openings against each other.

2. The anastomosis system of claim 1, wherein the one or more elongated members comprise a first elongated member and a second elongated member and the one or more engagement portions comprise a first engagement portion and a second engagement portion that everts the ring between the first configuration and the second configuration.

3. The anastomosis system of claim 2, wherein the first engagement portion engages a first peak of the ring and the second engagement portion engages a second peak of the ring during eversion.

4. The anastomosis system of claim 3, wherein the first elongated member and the second elongated member rotate to evert the ring while the first engagement portion engages the first peak of the ring and the second engagement portion engages the second peak of the ring.

5. The anastomosis system of claim 2, wherein the first engagement portion engages a first peak of the ring and the second engagement portion engages a first trough of the ring during eversion.

6. The anastomosis system of claim 5, wherein the first elongated member pulls the first peak of the ring and the second elongated member pushes the first trough of the ring to evert the ring when the first engagement portion engages the first peak of the ring and the second engagement portion engages the first trough of the ring.

7. The anastomosis system of claim 2, wherein the first engagement portion and the second engagement portion comprise a hook or a clamp.

8. The anastomosis system of claim 2, wherein the first engagement portion and the second engagement portion comprise a groove or a plurality of right angle fingers.

9. The anastomosis system of claim 1, wherein the ring further comprises a plurality of alternate peaks and troughs.

10. The anastomosis system of claim 1, wherein the one or more engagement portions comprise a rigid sleeve.

11. The anastomosis system of claim 10, wherein the rigid sleeve is positioned over a portion of the ring.

12. An anastomosis system, comprising:
a delivery device comprising one or more engagement portions; and
a ring having a plurality of peaks and troughs and a plurality of pins connected to the ring to form a tubular shape;
wherein the one or more engagement portions of the delivery device engage the ring through the plurality of peaks and troughs in a first configuration and evert the ring in a second configuration such that the plurality of peaks and troughs and the plurality of pins move inside out to form an inverted tubular shape between the first configuration and the second configuration.

13. The anastomosis system of claim 12, wherein the plurality of pins further comprises a first plurality of pins having a first length and a second plurality of pins having a second length.

14. The anastomosis system of claim 12, wherein the delivery device further comprises an elongated portion attached to each of the one or more engagement portions.

15. The anastomosis system of claim 14, wherein the elongated portion is rotated to evert the ring.

16. The anastomosis system of claim 15, wherein the elongated portion is rotated via a handle.

17. The anastomosis system of claim 12, wherein the one or more engagement portions of the delivery device engages the ring in a perpendicular orientation or a parallel orientation with respect to an orientation of the plurality of peaks and troughs.

18. The anastomosis system of claim 17, wherein a first engagement portion of the one or more engagement portions engages a first peak of the ring and a second engagement portion of the one or more engagement portions engages a second peak of the ring in the perpendicular orientation with respect to the orientation of the plurality of peaks and troughs.

19. The anastomosis system of claim 17, wherein a first engagement portion of the one or more engagement portions engages a first peak of the ring and a second engagement portion of the one or more engagement portions engages a first trough of the ring in the parallel orientation with respect to the orientation of the plurality of peaks and troughs.

20. An anastomosis system, comprising:
a delivery device, comprising:
one or more engagement portions; and
a connecting ring having a plurality of pins positioned on the connecting ring and the plurality of pins are configured to insert through tissue of two biological passages in a first direction;
wherein the delivery device is configured to evert the connecting ring through the one or more engagement portions such that the connecting ring and the plurality of pins move from the first direction to a second direction to form a tubular shape to press the tissue of two biological passages against each other.

* * * * *